(12) United States Patent
Yokoyama et al.

(10) Patent No.: US 9,196,837 B2
(45) Date of Patent: Nov. 24, 2015

(54) COMPOUND HAVING INDENOCARBAZOLE RING STRUCTURE, AND ORGANIC ELECTROLUMINESCENT DEVICE

(75) Inventors: Norimasa Yokoyama, Tokyo (JP); Makoto Nagaoka, Tsukuba (JP); Kazunori Togashi, Tokyo (JP); Kouki Kase, Tsukuba (JP); Eiji Takahashi, Tsukuba (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 366 days.

(21) Appl. No.: 13/812,995

(22) PCT Filed: Jul. 29, 2011

(86) PCT No.: PCT/JP2011/004334
§ 371 (c)(1),
(2), (4) Date: Jan. 29, 2013

(87) PCT Pub. No.: WO2012/014500
PCT Pub. Date: Feb. 2, 2012

(65) Prior Publication Data
US 2013/0126856 A1    May 23, 2013

(30) Foreign Application Priority Data

Jul. 30, 2010  (JP) ................. 2010-171657

(51) Int. Cl.
| | | |
|---|---|---|
| *H01L 51/00* | (2006.01) | |
| *C07D 209/70* | (2006.01) | |
| *C07D 209/86* | (2006.01) | |
| *C07D 401/10* | (2006.01) | |
| *C07D 403/10* | (2006.01) | |
| *C07D 403/14* | (2006.01) | |
| *C07D 409/10* | (2006.01) | |
| *C07D 413/10* | (2006.01) | |
| *C07D 417/14* | (2006.01) | |
| *C09B 57/00* | (2006.01) | |
| *H01L 51/50* | (2006.01) | |

(52) U.S. Cl.
CPC .......... *H01L 51/0053* (2013.01); *C07D 209/70* (2013.01); *C07D 209/86* (2013.01); *C07D401/10* (2013.01); *C07D 403/10* (2013.01); *C07D 403/14* (2013.01); *C07D 409/10* (2013.01); *C07D 413/10* (2013.01); *C07D 417/14* (2013.01); *C09B 57/00* (2013.01); *C09B 57/008* (2013.01); *H01L 51/0061* (2013.01); *H01L 51/0072* (2013.01); *H01L 51/0058* (2013.01); *H01L 51/0059* (2013.01); *H01L 51/5012* (2013.01); *H01L 51/5048* (2013.01); *H01L 51/5088* (2013.01); *H01L 51/5096* (2013.01)

(58) Field of Classification Search
None
See application file for complete search history.

(56) References Cited

U.S. PATENT DOCUMENTS

| | | | |
|---|---|---|---|
| 2006/0063033 A1* | 3/2006 | Sohn et al. | 428/690 |
| 2008/0220285 A1* | 9/2008 | Vestweber et al. | 428/690 |
| 2009/0066225 A1* | 3/2009 | Kimura et al. | 313/504 |
| 2009/0184313 A1* | 7/2009 | Buesing et al. | 257/40 |
| 2009/0261717 A1* | 10/2009 | Buesing et al. | 313/504 |
| 2010/0012931 A1 | 1/2010 | Kato et al. | |
| 2011/0037027 A1 | 2/2011 | Stoessel et al. | |
| 2012/0068170 A1 | 3/2012 | Pflumm et al. | |
| 2012/0238105 A1 | 9/2012 | Anemian et al. | |
| 2012/0292576 A1 | 11/2012 | Parham et al. | |
| 2012/0319052 A1 | 12/2012 | Brocke et al. | |
| 2012/0326141 A1 | 12/2012 | Pflumm et al. | |
| 2014/0048745 A1 | 2/2014 | Anemian et al. | |

FOREIGN PATENT DOCUMENTS

| | | |
|---|---|---|
| CN | 102448946 A | 5/2012 |
| JP | 2006-083386 A | 3/2006 |
| JP | 2009-227856 A | 10/2009 |
| JP | 2009-242746 A | 10/2009 |
| JP | 2010-040829 A | 2/2010 |
| JP | 2012-528088 A | 11/2012 |
| JP | 2013-504884 A | 2/2013 |

| | | | |
|---|---|---|---|
| JP | 2013-518068 A | 5/2013 | |
| JP | 2013-521238 A | 6/2013 | |
| JP | 2013-522864 A | 6/2013 | |
| JP | 2013-527989 A | 7/2013 | |
| WO | WO-2009/124627 A1 | 10/2009 | |
| WO | WO-2009/148062 A1 | 12/2009 | |
| WO | WO-2010/136109 A1 | 12/2010 | |

OTHER PUBLICATIONS

International Search Report dated Oct. 4, 2011, issued for PCT/JP2011/004334.
Office Action mailed Feb. 10, 2015, issued for the Japanese patent application No. 2012-526336.
Office Action dated Oct. 10, 2013, issued for the Chinese patent application No. 201180037353.3.
Supplementary European Search Report dated Nov. 22, 2013, issued for the European patent application No. 11812097.1.

* cited by examiner

*Primary Examiner* — Robert S Loewe
(74) *Attorney, Agent, or Firm* — Locke Lord LLP; James E. Armstrong, IV; Nicholas J. DiCeglie, Jr.

(57) ABSTRACT

An organic compound with excellent characteristics excelling in hole-injecting/transporting performance and having electron blocking ability, high stability in a thin-film state and high luminous efficiency is provided as material for an organic electroluminescent device.

The compound of a general formula (1) having an indenocarbazole ring structure is used as a constituent material of at least one organic layer in the organic electroluminescent device that includes a pair of electrodes and one or more organic layers sandwiched between the pair of electrodes.

[Chemical Formula 1]

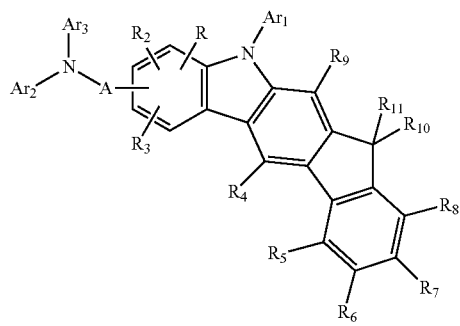

18 Claims, 5 Drawing Sheets

COMPOUND HAVING INDENOCARBAZOLE RING STRUCTURE, AND ORGANIC ELECTROLUMINESCENT DEVICE

TECHNICAL FIELD

The present invention relates to compounds suitable for an organic electroluminescent device which is a preferred self-luminous device for various display devices, and relates to the organic electroluminescent device. Specifically, this invention relates to compounds having an indenocarbazole ring structure, and organic electroluminescent devices using the compounds.

BACKGROUND ART

The organic electroluminescent device is a self-luminous device and has been actively studied for their brighter, superior visibility and the ability to display clearer images in comparison with liquid crystal devices.

In 1987, C. W. Tang and colleagues at Eastman Kodak developed a laminated structure device using materials assigned with different roles, realizing practical applications of an organic electroluminescent device with organic materials. These researchers laminated an electron-transporting phosphor which is tris(8-hydroxyquinoline)aluminum (hereinafter referred to as $Alq_3$) and a hole-transporting aromatic amine compound, and injected both charges into a phosphor layer to cause emission in order to obtain a high luminance of 1,000 cd/m$^2$ or more at a voltage of 10 V or less (refer to Patent Documents 1 and 2, for example).

To date, various improvements have been made for practical applications of the organic electroluminescent device. In order to realize high efficiency and durability, various roles are further subdivided to provide an electroluminescence device that includes an anode, a hole injection layer, a hole transport layer, a light emitting layer, an electron transport layer, an electron injection layer, and a cathode successively formed on a substrate (refer to Non-Patent Document 1, for example).

Further, there have been attempts to use triplet excitons for further improvements of luminous efficiency, and the use of phosphorescent materials has been examined (refer to Non-Patent Document 2, for example).

The light emitting layer can be also fabricated by doping a charge-transporting compound generally called a host material, with a phosphor or a phosphorescent material. As described in the foregoing lecture preprints, the selection of organic materials in an organic electroluminescent device greatly influences various device characteristics such as efficiency and durability.

In an organic electroluminescent device, charges injected from both electrodes recombine in a light emitting layer to cause emission. What is important here is how efficiently the hole and electron charges are transferred to the light emitting layer. The probability of hole-electron recombination can be improved by improving hole injectability and electron blocking performance of blocking injected electrons from the cathode, and high luminous efficiency can be obtained by confining excitons generated in the light emitting layer. The role of a hole transport material is therefore important, and there is a need for a hole transport material that has high hole injectability, high hole mobility, high electron blocking performance, and high durability to electrons.

Heat resistance and amorphousness of the materials are also important with respect to a lifetime of the device. The materials with low heat resistance cause thermal decomposition even at a low temperature by heat generated during the drive of the device, which leads to the deterioration of the materials. The materials with low amorphousness cause crystallization of a thin film even in a short time and lead to the deterioration of the device. The materials in use are therefore required to have characteristics of high heat resistance and satisfactory amorphousness.

N,N'-diphenyl-N,N'-di(α-naphthyl)benzidine (hereinafter referred to as NPD) and various aromatic amine derivatives are known as the hole transport materials used for the organic electroluminescent device (refer to Patent Documents 1 and 2, for example). Although NPD has desirable hole transportability, the glass transition point (Tg), which is an index of heat resistance, is as low as 96° C., which causes the degradation of device characteristics by crystallization under high-temperature conditions (refer to Non-Patent Document 3, for example). The aromatic amine derivatives described in the Patent Documents 1 and 2 include a compound known to have an excellent hole mobility of $10^{-3}$ cm$^2$/Vs or higher. However, since the compound is insufficient in terms of electron blocking performance, some of the electrons pass through the light emitting layer, and improvements in luminous efficiency cannot be expected. For such a reason, a material with higher electron blocking performance, a more stable thin-film state and higher heat resistance is needed for higher efficiency.

Arylamine compounds of the following formulae having a substituted carbazole structure (for example, Compounds A and B) are proposed as compounds improved in the characteristics such as heat resistance and hole injectability (refer to Patent Documents 3 and 4, for example).

[Chemical Formula 1]

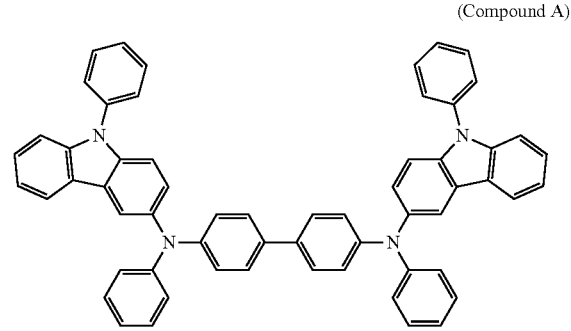

(Compound A)

[Chemical Formula 2]

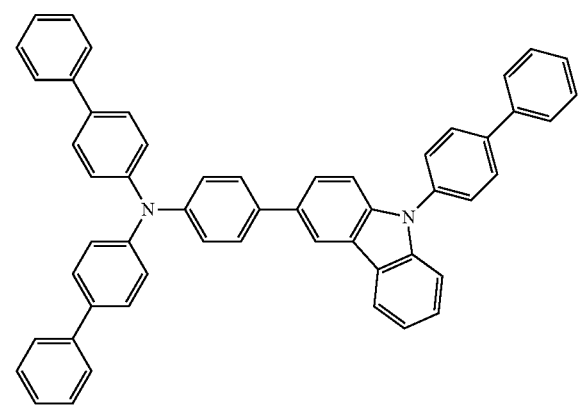

(Compound B)

However, while the devices using these compounds for the hole injection layer or the hole transport layer have been improved in heat resistance, luminous efficiency, and the like, the improvements are still insufficient. Further, the devices have neither sufficiently low driving voltage nor sufficient current efficiency. Further improvements of a low driving voltage and luminous efficiency are therefore needed.

CITATION LIST

Patent Documents

Patent Document 1: JP-A-8-048656
Patent Document 2: Japanese Patent No. 3194657
Patent Document 3: JP-A-2006-151979
Patent Document 4: WO2008/62636

Non-Patent Documents

Non-Patent Document 1: The Japan Society of Applied Physics, 9th Lecture Preprints, pp. 55 to 61 (2001)
Non-Patent Document 2: The Japan Society of Applied Physics, 9th Lecture Preprints, pp. 23 to 31 (2001)
Non-Patent Document 3: Organic EL Symposium, the 3rd Regular presentation Preprints, pp. 13 to 14 (2006)
Non-Patent Document 4: J. Org. Chem., 60, 7508 (1995)
Non-Patent Document 5: Synth. Commun., 11, 513 (1981)

SUMMARY OF THE INVENTION

Problems to be Solved by the Invention

An object of the present invention is to provide an organic compound with excellent characteristics excelling in hole-injecting/transporting performance and having electron blocking ability, high stability in a thin-film state and high luminous efficiency, the organic compound being provided as material for an organic electroluminescent device having high efficiency and high durability. This invention also provides the organic electroluminescent device of high efficiency and high durability using this compound.

Physical properties of the organic compound to be provided by the present invention include (1) good hole injection characteristics, (2) large hole mobility, (3) excellent electron blocking ability, (4) stability in the thin-film state, and (5) excellent heat resistance. Physical properties of the organic electroluminescent device to be provided by the present invention include (1) high luminous efficiency and high power efficiency, (2) low turn on voltage, and (3) low actual driving voltage.

Means of Solving the Problems

In order to achieve the above objects, the present inventors focused on the planeness of an indenocarbazole ring structure which can be expected to provide high hole mobility, a high triplet energy level, excellent electron blocking performance, and furthermore excellent heat resistance and thin-film stability, and also focused on the high hole-injecting/transporting ability of an aromatic tertiary amine structure to design compounds having the indenocarbazole ring structure and the aromatic tertiary amine structure. The present inventors produced various test organic electroluminescent devices using the compounds chemically synthesized to have the indenocarbazole ring structure and the aromatic tertiary amine structure, and completed the present invention after thorough evaluations of the device characteristics.

Specifically, the present invention is a compound of the following general formula (1) having an indenocarbazole ring structure.

[Chemical Formula 3]

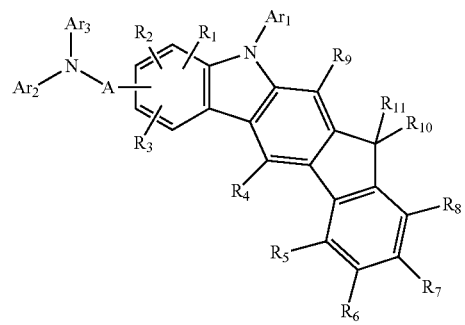

(1)

In the formula, A represents a divalent group of a substituted or unsubstituted aromatic hydrocarbon, a divalent group of a substituted or unsubstituted aromatic heterocyclic ring, or a divalent group of substituted or unsubstituted condensed polycyclic aromatics. $Ar_1$, $Ar_2$, and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group. A and $Ar_2$, or $Ar_2$ and $Ar_3$ may bind to each other via a single bond or via substituted or unsubstituted methylene, an oxygen atom, or a sulfur atom to form a ring. $R_1$ to $R_9$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring. $R_{10}$ and $R_{11}$ may be the same or different, and represent linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

Further, the present invention is a compound of the following general formula (2) having an indenocarbazole ring structure.

[Chemical Formula 4]

(2)

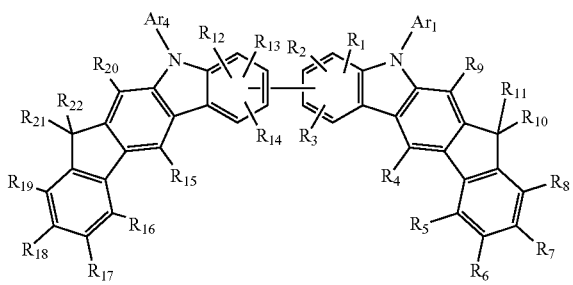

In the formula, $Ar_1$ and $Ar_4$ may be the same or different, and represent a substituted or unsubstituted aromatic hydrocarbon group, a substituted or unsubstituted aromatic heterocyclic group, or a substituted or unsubstituted condensed polycyclic aromatic group. $R_1$ to $R_9$ and $R_{12}$ to $R_{20}$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring. $R_{10}$, $R_{11}$, $R_{21}$, and $R_{22}$ may be the same or different, and represent linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where $R_{10}$ and $R_{11}$, or $R_{21}$ and $R_{22}$ may bind to each other via a single bond, substituted or unsubstituted methylene, an oxygen atom, or a sulfur atom to form a ring.

Further, the present invention is a compound of the following general formula (3) having an indenocarbazole ring structure.

[Chemical Formula 5]

(3)

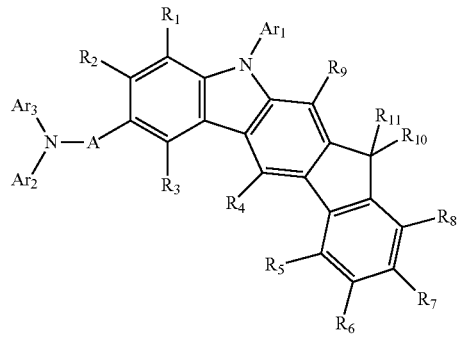

In the formula, A represents a divalent group of a substituted or unsubstituted aromatic hydrocarbon, a divalent group of a substituted or unsubstituted aromatic heterocyclic ring, or a divalent group of substituted or unsubstituted condensed polycyclic aromatics. $Ar_1$, $Ar_2$, and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group. A and $Ar_2$, or $Ar_2$ and $Ar_3$ may bind to each other via a single bond or via substituted or unsubstituted methylene, an oxygen atom, or a sulfur atom to form a ring. $R_1$ to $R_9$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring. $R_{10}$ and $R_{11}$ may be the same or different, and represent linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

Further, the present invention is a compound of the following general formula (4) having an indenocarbazole ring structure.

[Chemical Formula 6]

(4)

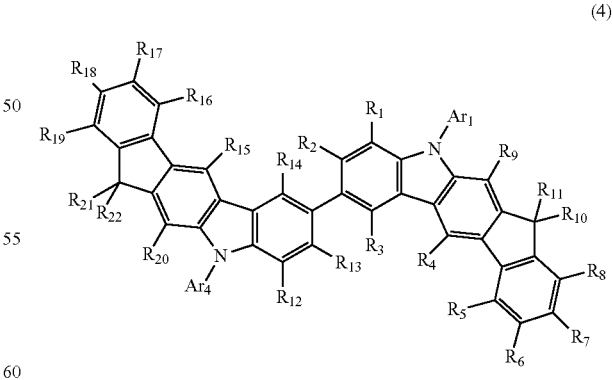

In the formula, $Ar_1$ and $Ar_4$ may be the same or different, and represent a substituted or unsubstituted aromatic hydrocarbon group, a substituted or unsubstituted aromatic heterocyclic group, or a substituted or unsubstituted condensed polycyclic aromatic group. $R_1$ to $R_9$ and $R_{12}$ to $R_{20}$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring. $R_{10}$, $R_{11}$, $R_{21}$, and $R_{22}$ may be the same or different, and represent linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where $R_{10}$ and $R_{11}$, or $R_{21}$ and $R_{22}$ may bind to each other via a single bond, substituted or unsubstituted methylene, an oxygen atom, or a sulfur atom to form a ring.

Further, the present invention is an organic electroluminescent device that includes a pair of electrodes and one or more organic layers sandwiched between the pair of electrodes, wherein the compound of any one of the general formulae (1) to (4) having an indenocarbazole ring structure is used as a constituent material of at least one organic layer.

Specific examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_1$ to $R_{22}$ in general formulae (1) to (4), can be methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. These groups may bind to each other via a single bond, substituted or unsubstituted methylene, an oxygen atom, or a sulfur atom to form a ring.

Specific examples of the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_1$ to $R_{22}$ in general formulae (1) to (4) can be a deuterium atom; cyano; nitro; halogen atoms such as a fluorine atom, a chlorine atom, a bromine atom, and an iodine atom; linear or branched alkoxys of 1 to 6 carbon atoms such as methoxy, ethoxy, and propyloxy; alkenyls such as allyl; aryloxys such as phenoxy and tolyloxy; arylalkoxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; and aromatic heterocyclic groups such as pyridyl, furanyl, pyranyl, thienyl, furyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl. These substituents may be further substituted with other substituents. These substituents may bind to each other via a single bond, substituted or unsubstituted methylene, an oxygen atom, or a sulfur atom to form a ring.

Specific examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_1$ to $R_{22}$ in general formulae (1) to (4) can be methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy. These groups may bind to each other via a single bond, substituted or unsubstituted methylene, an oxygen atom, or a sulfur atom to form a ring.

Specific examples of the "substituent" in the "linear or branched alkyloxy of 1 to 6 carbon atoms that has a substituent" or the "cycloalkyloxy of 5 to 10 carbon atoms that has a substituent" represented by $R_1$ to $R_{22}$ in general formulae (1) to (4) can be a deuterium atom; cyano; nitro; halogen atoms such as a fluorine atom, a chlorine atom, a bromine atom, and an iodine atom; linear or branched alkoxys of 1 to 6 carbon atoms such as methoxy, ethoxy, and propyloxy; alkenyls such as allyl; aryloxys such as phenoxy and tolyloxy; arylalkoxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; and aromatic heterocyclic groups such as pyridyl, furanyl, pyranyl, thienyl, furyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl. These substituents may be further substituted with other substituents. These substituents may bind to each other via a single bond, substituted or unsubstituted methylene, an oxygen atom, or a sulfur atom to form a ring.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_1$ to $R_{22}$ and $Ar_1$ to $Ar_4$ in general formulae (1) to (4) can be phenyl, biphenylyl, terphenylyl, naphthyl, anthryl, phenanthryl, fluorenyl, indenyl, pyrenyl, perylenyl, fluoranthenyl, triphenylenyl, pyridyl, furanyl, pyranyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl. These groups may bind to each other via a single bond, substituted or unsubstituted methylene, an oxygen atom, or a sulfur atom to form a ring.

It is preferable that the "aromatic heterocyclic group" in the "substituted or unsubstituted aromatic heterocyclic group" represented by $Ar_2$ to $Ar_4$ in general formulae (1) to (4) be a sulfur-containing aromatic heterocyclic group such as thienyl, benzothienyl, benzothiazolyl, or dibenzothienyl.

With respect to the bonding position of the "substituted or unsubstituted aromatic heterocyclic group" represented by $R_1$ to $R_{22}$ and $Ar_1$ in general formulae (1) to (4), it is preferable to bond with a carbon atom of the "aromatic heterocyclic group" from the viewpoint of stability and heat resistance.

Specific examples of the "substituent" in the "substituted aromatic hydrocarbon group", the "substituted aromatic heterocyclic group", or the "substituted condensed polycyclic aromatic group" represented by $R_1$ to $R_{22}$ and $Ar_1$ to $Ar_4$ in general formulae (1) to (4) can be a deuterium atom; trifluoromethyl; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkoxys of 1 to 6 carbon atoms such as methoxy, ethoxy, and propyloxy; alkenyls such as allyl; aralkyls such as benzyl, naphthylmethyl, and phenethyl; aryloxys such as phenoxy and tolyloxy; arylalkoxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, furanyl, pyranyl, thienyl, furyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl and benzoyl; dialkylamino groups such as dimethylamino and diethylamino; disubstituted amino groups such as diphenylamino and dinaphthylamino, substituted with aromatic hydrocarbon groups or condensed polycyclic aromatic groups; diaralkylamino groups such as dibenzylamino and diphenethylamino; disubstituted amino groups such as dipyridylamino and dithienylamino, substituted with aromatic heterocyclic groups; dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted. These substituents may bind to each other via a single bond, substituted or unsubstituted methylene, an oxygen atom, or a sulfur atom to form a ring.

Specific examples of the "aryloxy" in the "substituted or unsubstituted aryloxy" represented by $R_1$ to $R_{22}$ in general formulae (1) to (4) can be phenoxy, biphenylyloxy, terphenylyloxy, naphthyloxy, anthryloxy, phenanthryloxy, fluorenyloxy, indenyloxy, pyrenyloxy, and perylenyloxy. These groups may bind to each other via a single bond, substituted or unsubstituted methylene, an oxygen atom or a sulfur atom to form a ring.

Specific examples of the "substituent" in the "substituted aryloxy" represented by $R_1$ to $R_{22}$ in general formulae (1) to (4) can be a deuterium atom; trifluoromethyl; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkoxys of 1 to 6 carbon atoms such as methoxy, ethoxy, and propyloxy; alkenyls such as allyl; aralkyls such as benzyl, naphthylmethyl, and phenethyl; aryloxys such as phenoxy and tolyloxy; arylalkoxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, furanyl, pyranyl, thienyl, furyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl and benzoyl; dialkylamino groups such as dimethylamino and diethylamino; disubstituted amino groups such as diphenylamino and dinaphthylamino, substituted with aromatic hydrocarbon groups or condensed polycyclic aromatic groups; diaralkylamino groups such as dibenzylamino and diphenethylamino; disubstituted amino groups such as dipyridylamino and dithienylamino, substituted with aromatic heterocyclic groups; dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted. These substituents may bind to each other via a single bond, substituted or unsubstituted methylene, an oxygen atom, or a sulfur atom to form a ring.

Specific examples of the "divalent group of an aromatic hydrocarbon", the "divalent group of an aromatic heterocyclic ring", or the "divalent group of condensed polycyclic aromatics" in the "divalent group of a substituted or unsubstituted aromatic hydrocarbon", the "divalent group of a substituted or unsubstituted aromatic heterocyclic ring", or the "divalent group of substituted or unsubstituted condensed polycyclic aromatics" represented by A in general formulae (1) and (3) can be phenylene, biphenylene, terphenylene, tetrakisphenylene, naphthylene, anthrylene, phenanthrylene, fluorenylene, phenanthrolylene, indenylene, pyrenylene, perylenylene, fluoranthenylene, triphenylenylene, pyridinylene, pyrimidinylene, quinolylene, isoquinolylene, indolylene, carbazolylene, quinoxalylene, benzoimidazolylene, pyrazolylene, naphthyridinylene, phenanthrolinylene, acridinylene, thienylene, benzothienylene, benzothiazolylene, and dibenzothienylene.

It is preferable that the "divalent group of an aromatic heterocyclic ring" in the "divalent group of a substituted or unsubstituted aromatic heterocyclic ring" represented by A in general formulae (1) and (3) be a divalent group of a sulfur-containing aromatic heterocyclic ring such as thienylene, benzothienylene, benzothiazolylene, or dibenzothienylene.

These groups may bind to the "substituted or unsubstituted aromatic hydrocarbon group", the "substituted or unsubstituted aromatic heterocyclic group", or the "substituted or unsubstituted condensed polycyclic aromatic group" represented by $Ar_2$ in general formulae (1) and (3), via a single bond, substituted or unsubstituted methylene, an oxygen atom, or a sulfur atom to form a ring.

Specific examples of the "substituent" in the "divalent group of a substituted aromatic hydrocarbon", the "divalent group of a substituted aromatic heterocyclic ring", or the "divalent group of substituted condensed polycyclic aromatics" represented by A in general formulae (1) and (3) can be a deuterium atom; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkoxys of 1 to 6 carbon atoms such as methoxy, ethoxy, and propyloxy; alkenyls such as allyl; aralkyls such as benzyl, naphthylmethyl, and phenethyl; aryloxys such as phenoxy and tolyloxy; arylalkoxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, furanyl, pyranyl, thienyl, furyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyls such as styryl and naphthylvinyl; and acyls such as acetyl and benzoyl. These substituents may be further substituted. These substituents may bind to each other via a single bond, substituted or unsubstituted methylene, an oxygen atom, or a sulfur atom to form a ring.

Among the compounds of the general formula (3) having an indenocarbazole ring structure, the compounds of the following general formula (3-1), (3-2), (3-3), or (3-4) having an indenocarbazole ring structure are preferably used for an organic electroluminescent device.

[Chemical Formula 7]

(3-1)

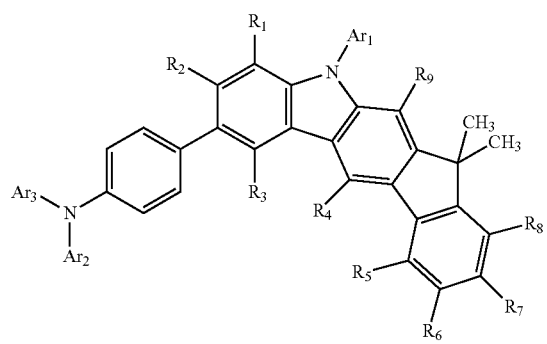

In the formula, $Ar_1$, $Ar_2$, and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group. $R_1$ to $R_9$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

[Chemical Formula 8]

(3-2)

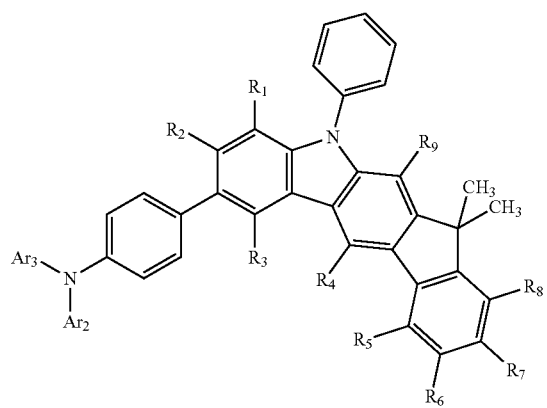

In the formula, $Ar_2$ and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group. $R_1$ to $R_9$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

[Chemical Formula 9]

(3-3)

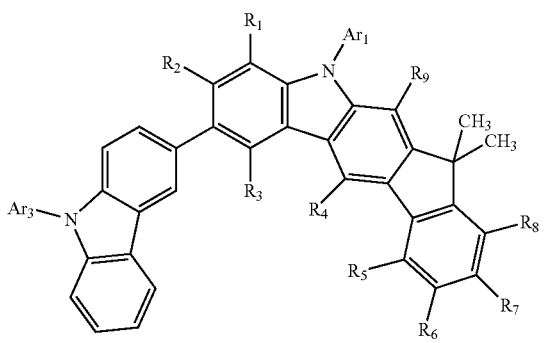

In the formula, $Ar_1$ and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group. $R_1$ to $R_9$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

[Chemical Formula 10]

(3-4)

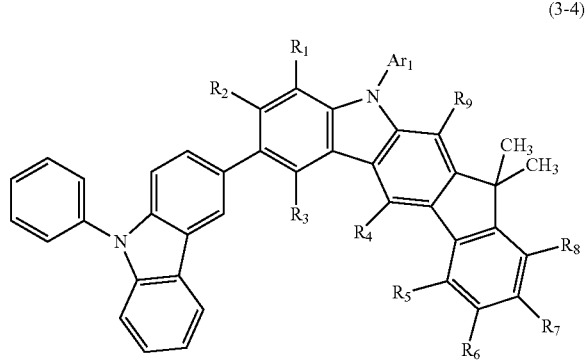

In the formula, $Ar_1$ represents a substituted or unsubstituted aromatic hydrocarbon group, a substituted or unsubstituted aromatic heterocyclic group, or a substituted or unsubstituted condensed polycyclic aromatic group. $R_1$ to $R_9$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

The compounds of general formula (1) having an indenocarbazole ring structure of the present invention are novel compounds and have superior electron blocking ability, superior amorphousness and a more stable thin-film state compared to conventional hole transport materials.

The compounds of general formula (1) having an indenocarbazole ring structure of the present invention can be used as a constituent material of the hole injection layer and/or hole transport layer of an organic electroluminescent device (hereinafter referred to as an organic EL device). With the use of material having higher hole injectability, higher mobility, higher electron blocking performance and higher stability to electrons than conventional materials, excitons generated in a light emitting layer can be confined, and the probability of hole-electron recombination can be improved. This improves luminous efficiency, lowers driving voltage and thus improves the durability of the organic EL device.

The compounds of general formula (1) having an indenocarbazole ring structure of the present invention can also be used as a constituent material of the electron blocking layer of an organic EL device. With the use of material having an excellent electron blocking ability and having superior hole transportability and higher stability in a thin-film state than conventional materials, driving voltage is lowered and current resistance is improved while maintaining high luminous efficiency. As a result, the maximum emission luminance of the organic EL device is improved.

The compounds of general formula (1) having an indenocarbazole ring structure of the present invention can also be used as a constituent material of the light emitting layer of the organic EL device. The material of the present invention having superior hole transportability and a wider band gap than conventional materials is used as the host material of the light emitting layer in order to form the light emitting layer by carrying a fluorescent material or phosphorescent material called a dopant. In this way, the organic EL device with a low driving voltage and improved luminous efficiency can be achieved.

The high efficiency and high durability of the organic EL device in the present invention can be achieved because of the use of the compound having an indenocarbazole ring structure, which has greater hole mobility, superior electron blocking ability, superior amorphousness, and a more stable thin-film state than conventional hole transport materials.

Effects of the Invention

The compound having an indenocarbazole ring structure of the present invention is useful as the constituent material of the hole injection layer, hole transport layer, electron blocking layer, or light emitting layer of the organic EL device. The compound excels in electron blocking ability, has an excellent electron blocking ability and satisfactory amorphousness, and excels in heat resistance as well as a stable thin-film state. The organic EL device of the present invention has high luminous efficiency and high power efficiency, and the actual driving voltage of the device can thereby be lowered. The turn on voltage can be lowered to improve durability.

MODE FOR CARRYING OUT THE INVENTION

Figure 1:
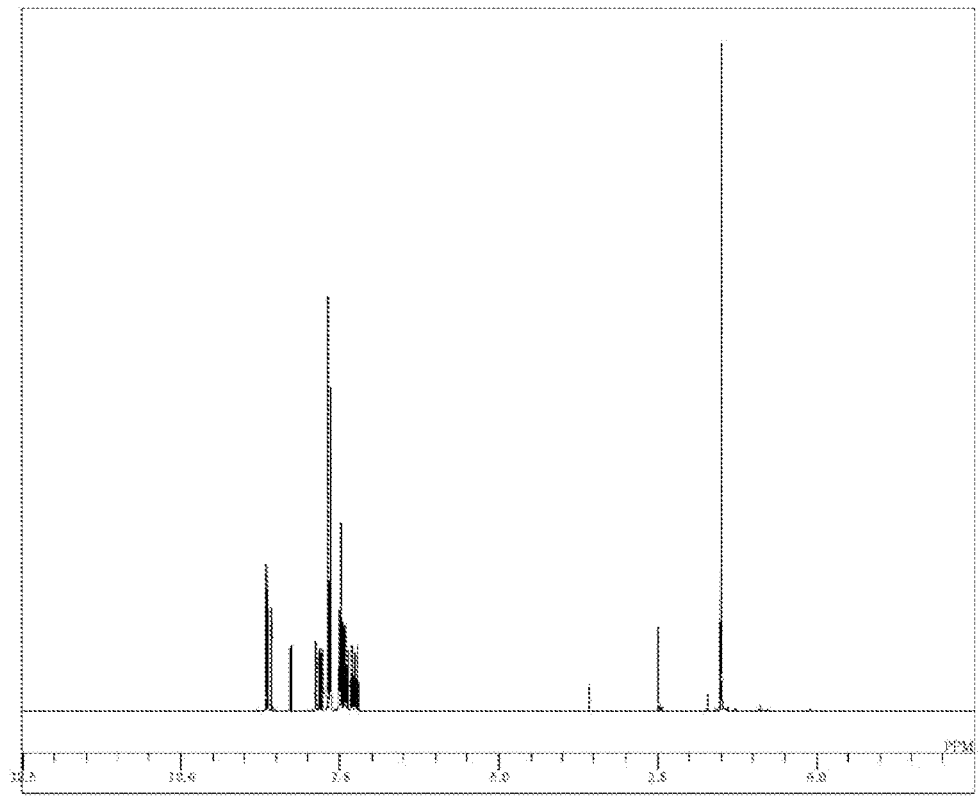
FIG. 1 is a 1H-NMR chart of the compound of Example 1 of the present invention (Compound 5).

The compounds having an indenocarbazole ring structure of the present invention are novel compounds, and may be synthesized, for example, as follows. For example, N-(9,9-dimethylfluorene-2-yl)-2-bromoaniline is synthesized by the reaction of 2-bromoaniline with 9,9-dimethyl-2-iodofluorene, and 12,12-dimethyl-10,12-dihydro-indeno[2,1-b]carbazole can be synthesized by subjecting the N-(9,9-dimethylfluorene-2-yl)-2-bromoaniline to a cyclization reaction. 12,12-Dimethyl-10-phenyl-10,12-dihydroindeno[2,1-b]carbazole can be synthesized by the condensation reaction (such as Ullmann reaction) of the 12,12-dimethyl-10,12-dihydroindeno[2,1-b]carbazole with iodobenzene. Further, 7-bromo-12,12-dimethyl-10-phenyl-10,12-dihydroindeno[2,1-b]carbazole can be synthesized by the bromination of the 12,12-dimethyl-10-phenyl-10,12-dihydroindeno[2,1-b]carbazole, using, for example, N-bromosuccinimide. A bromo-substituted compound of 10,12-dihydroindeno[2,1-b]carbazole substituted with a corresponding substituent can be synthesized by using, as a raw material, 2-bromoaniline, 2-iodofluorene, or an iodine compound, each of which is substituted with a corresponding substituent.

Boronic acid or borate synthesized by the reaction between aryl halides substituted with various diarylamino groups, and compounds such as pinacolborane and bis(pinacolato)diboron (refer to Non-Patent Document 4, for example) can then be reacted with the bromo-substituted compound of the 10,12-dihydroindeno[2,1-b]carbazole substituted with a corresponding substituent, in a cross-coupling reaction such as Suzuki coupling (refer to Non-Patent Document 5, for example) to synthesize the compounds having an indenocarbazole ring structure of the present invention.

The following presents specific examples of preferred compounds among the compounds of general formula (1) having an indenocarbazole ring structure. The present invention, however, is not restricted to these compounds.

[Chemical Formula 11] (Compound 5)
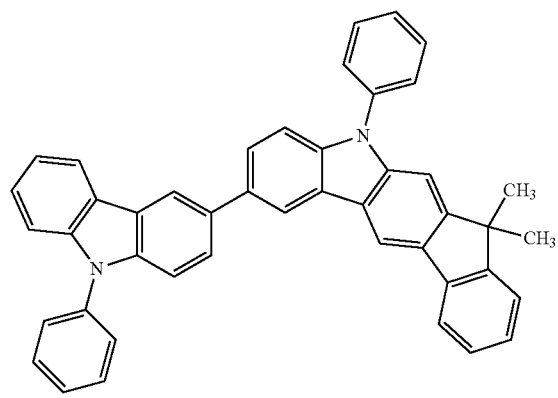
[Chemical Formula 12] (Compound 6)
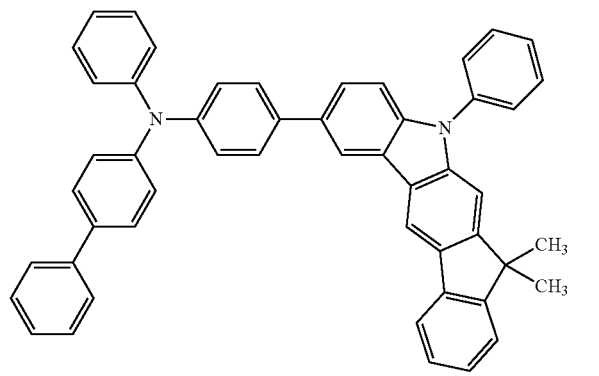
[Chemical Formula 13] (Compound 7)
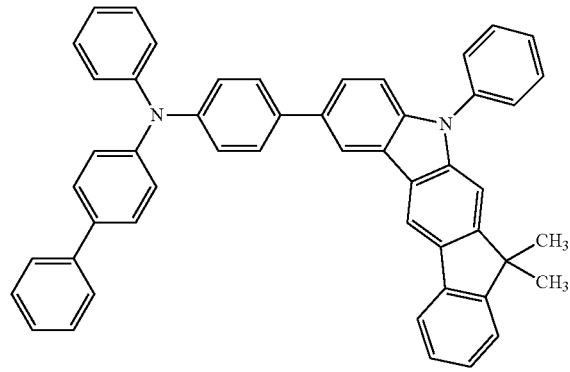
[Chemical Formula 14] (Compound 8)
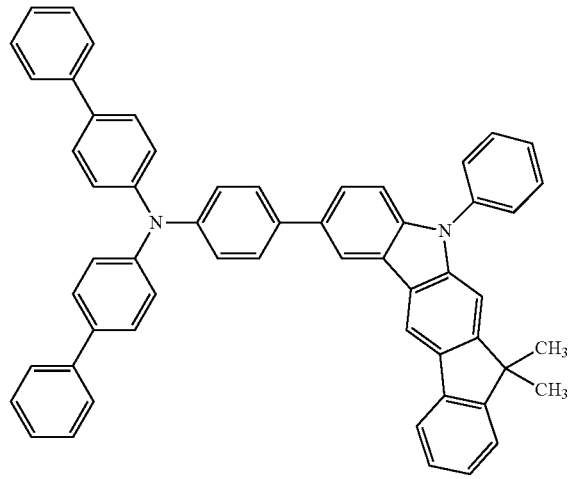
[Chemical Formula 15] (Compound 9)
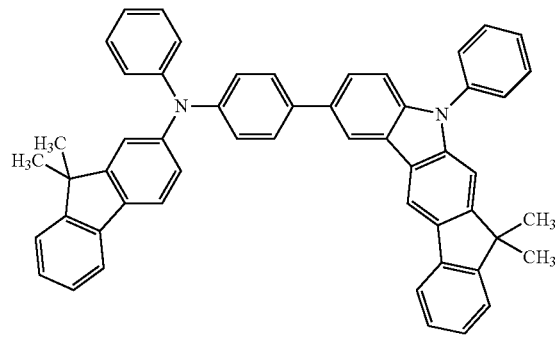
[Chemical Formula 16] (Compound 10)
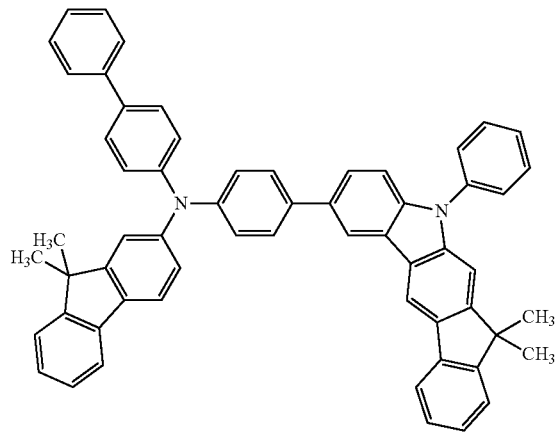

-continued
[Chemical Formula 17]
(Compound 11)
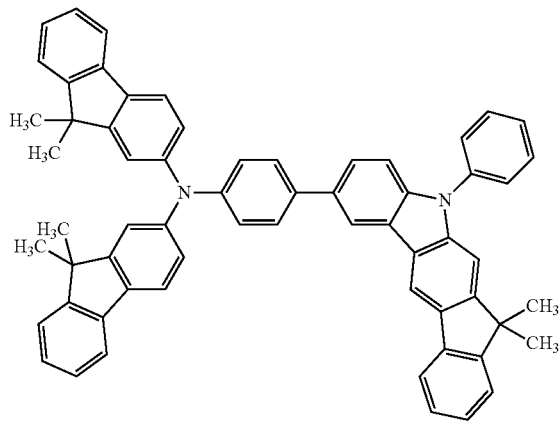
[Chemical Formula 18]
(Compound 12)
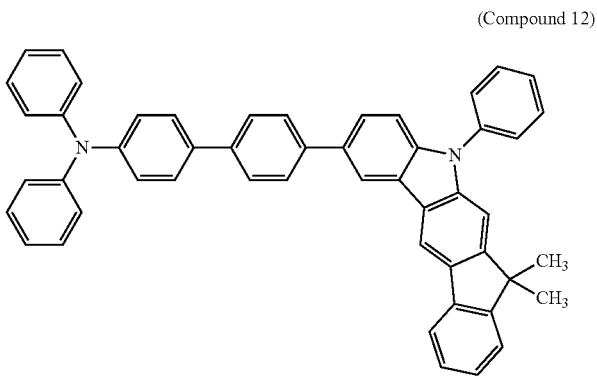
[Chemical Formula 19]
(Compound 13)
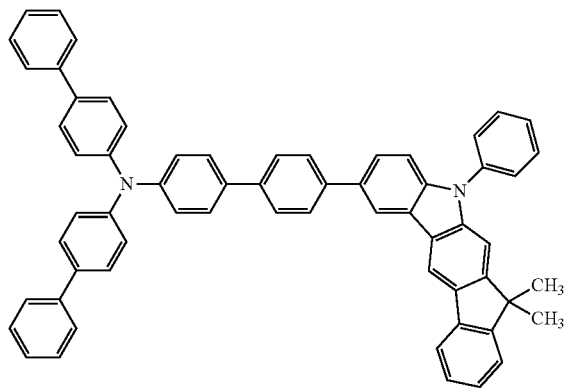
[Chemical Formula 20]
(Compound 14)
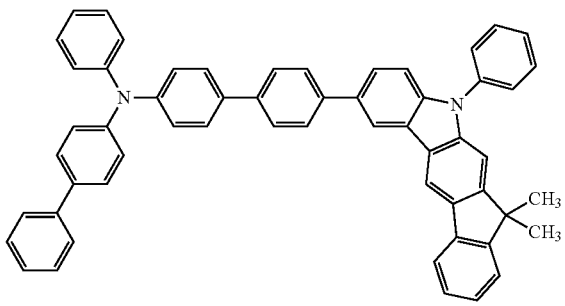
[Chemical Formula 21]
(Compound 15)
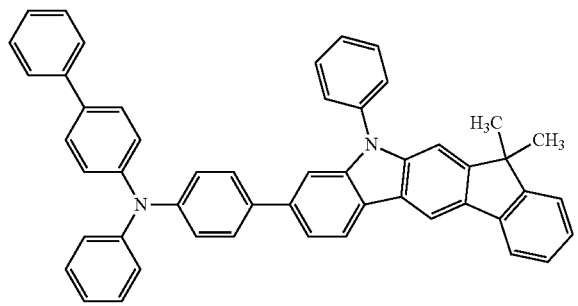
[Chemical Formula 22]
(Compound 16)
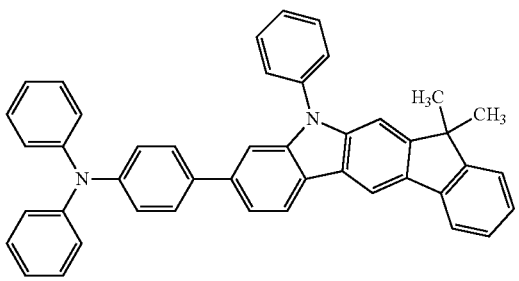

-continued
[Chemical Formula 23]
(Compound 17)
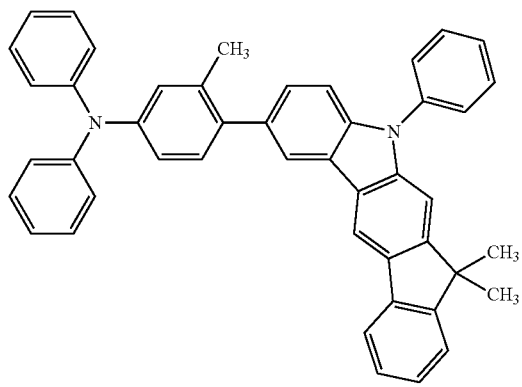
[Chemical Formula 24]
(Compound 18)
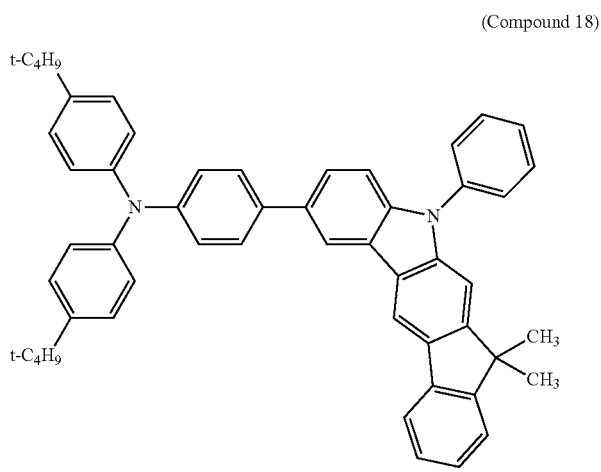
[Chemical Formula 25]
(Compound 19)
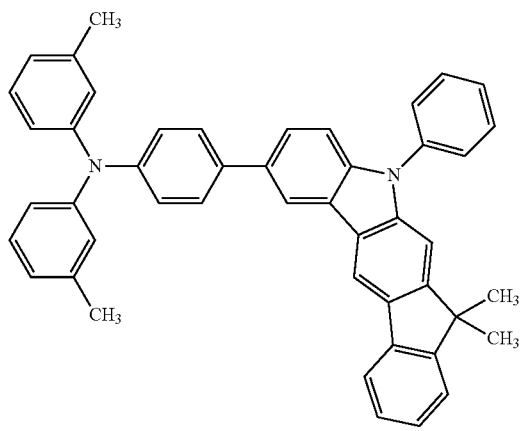
[Chemical Formula 26]
(Compound 20)
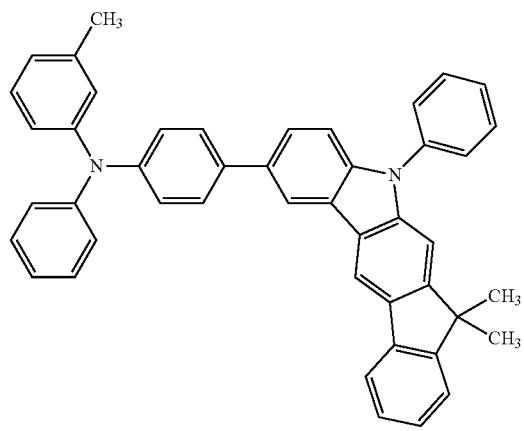
[Chemical Formula 27]
(Compound 21)
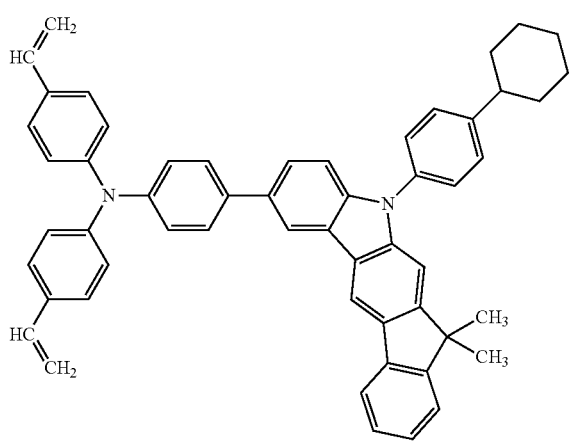
[Chemical Formula 28]
(Compound 22)
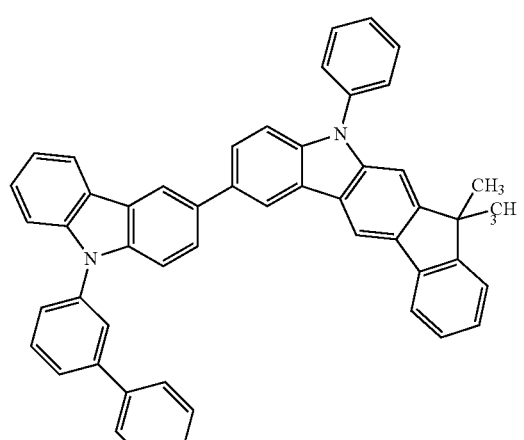

[Chemical Formula 29]
(Compound 23)
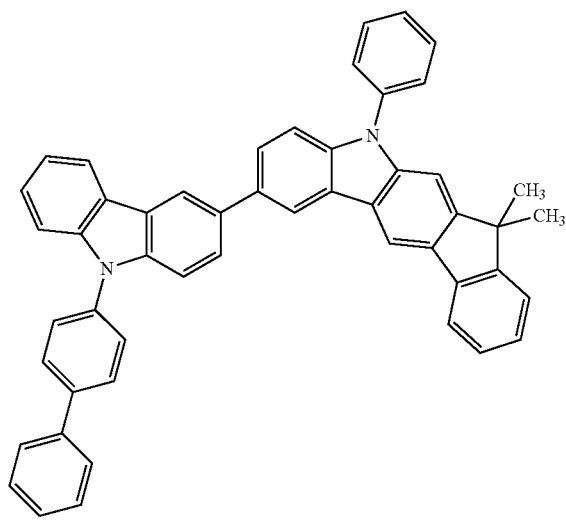
[Chemical Formula 30]
(Compound 24)
[Chemical Formula 31]
(Compound 25)
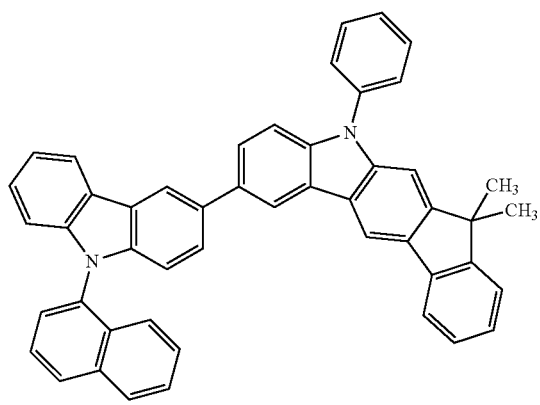
[Chemical Formula 32]
(Compound 26)
[Chemical Formula 33]
(Compound 27)
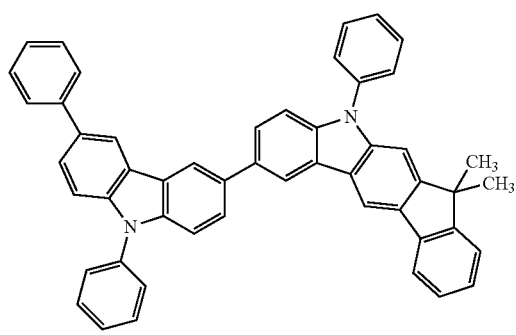
[Chemical Formula 34]
(Compound 28)
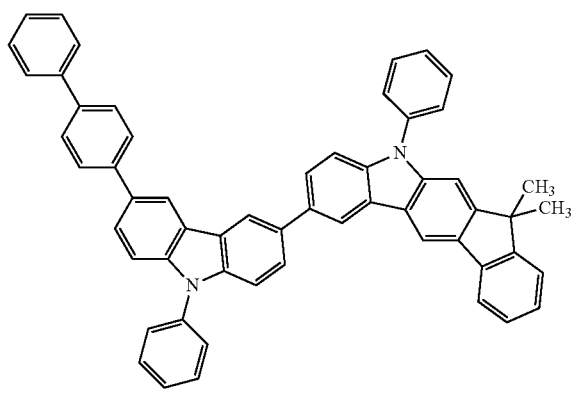

-continued
[Chemical Formula 35]
(Compound 29)
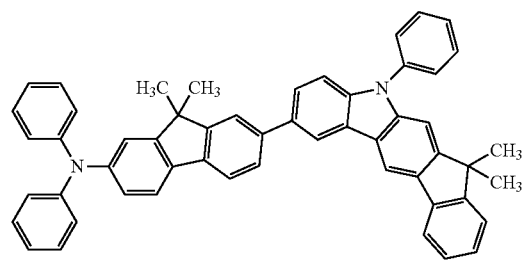
[Chemical Formula 36]
(Compound 30)
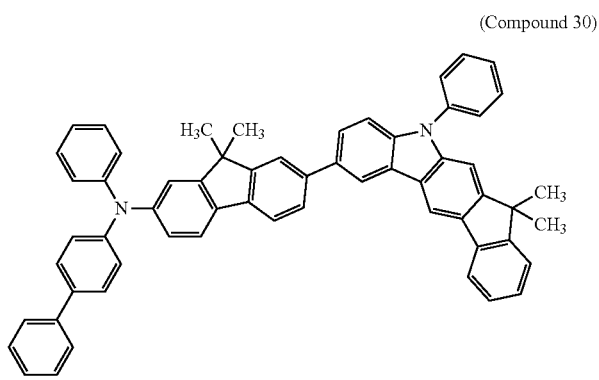
[Chemical Formula 37]
(Compound 31)
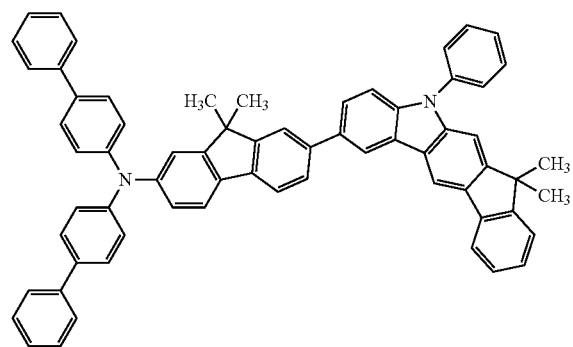
[Chemical Formula 38]
(Compound 32)
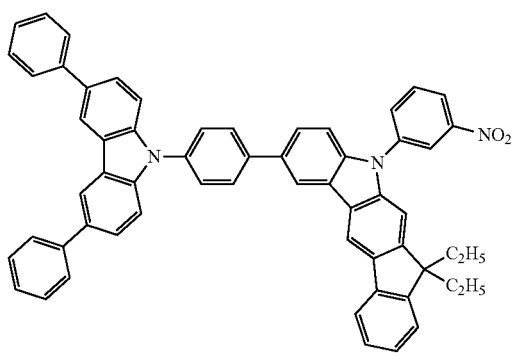
[Chemical Formula 39]
(Compound 33)
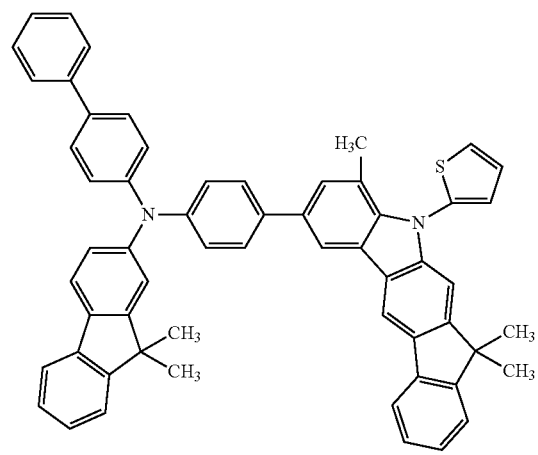
[Chemical Formula 40]
(Compound 34)
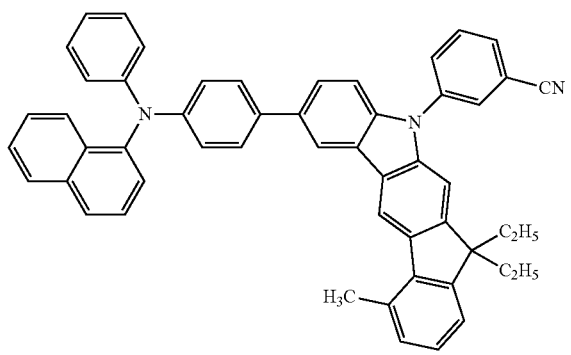

[Chemical Formula 41]
(Compound 35)
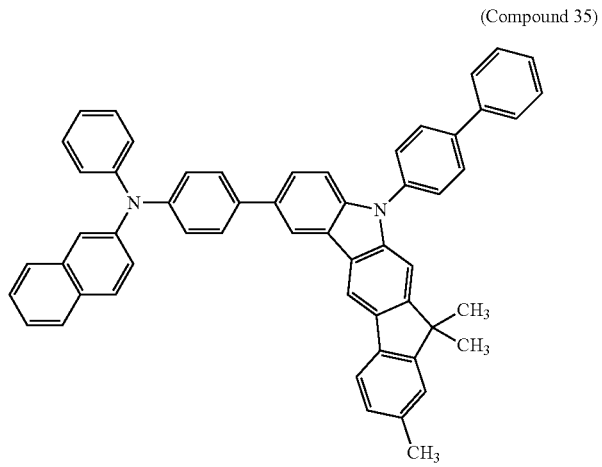
[Chemical Formula 42]
(Compound 36)
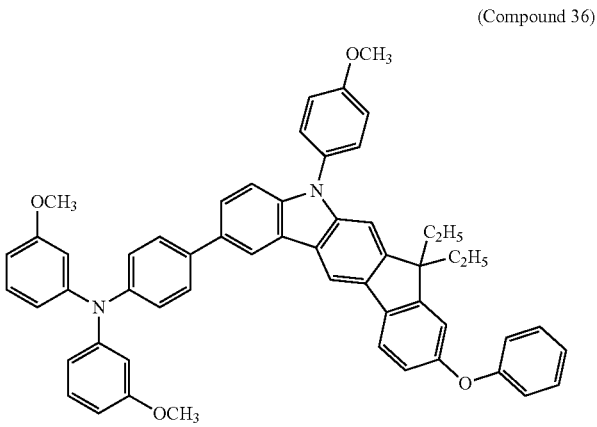
[Chemical Formula 43]
(Compound 37)
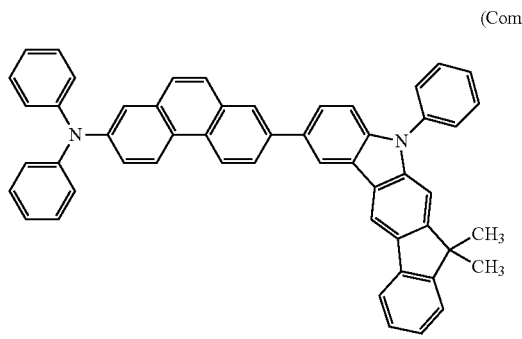
[Chemical Formula 44]
(Compound 38)
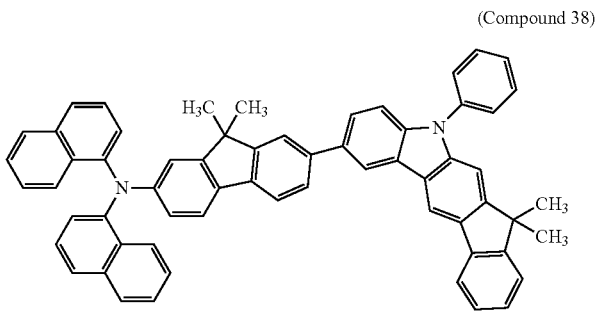
[Chemical Formula 45]
(Compound 39)
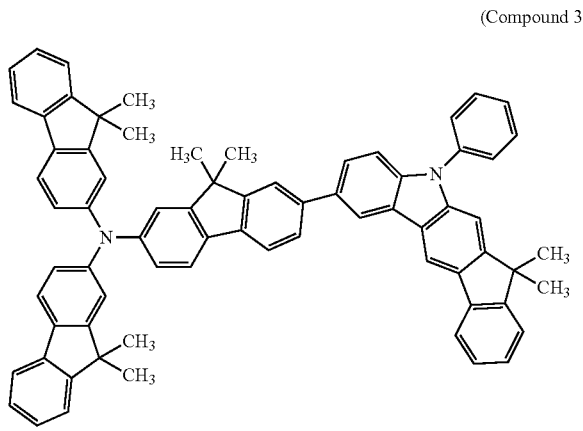
[Chemical Formula 46]
(Compound 40)
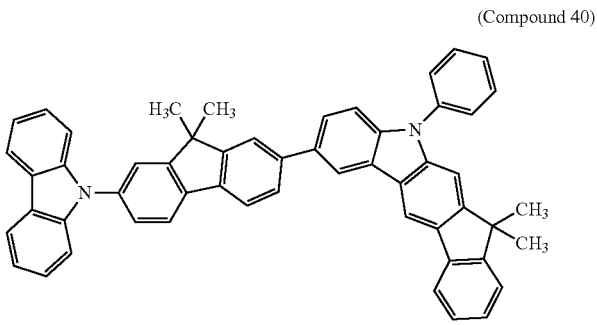

-continued
[Chemical Formula 47]
(Compound 41)
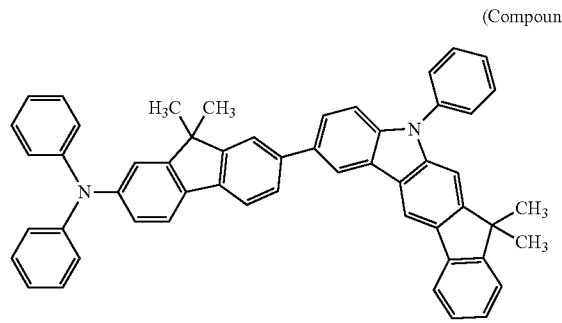
[Chemical Formula 48]
(Compound 42)
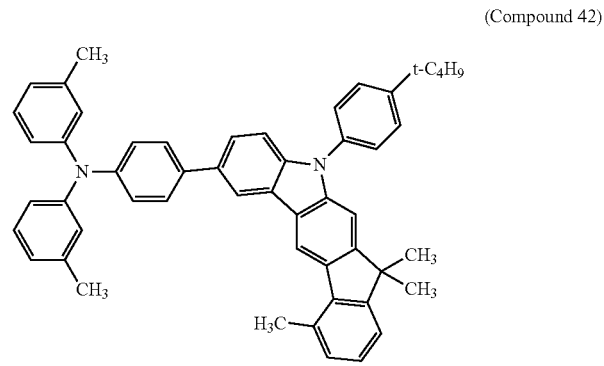
[Chemical Formula 49]
(Compound 43)
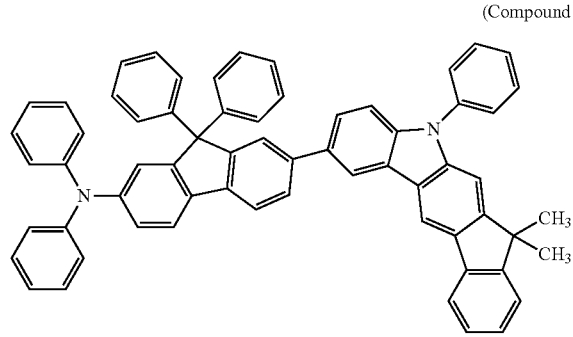
[Chemical Formula 50]
(Compound 44)
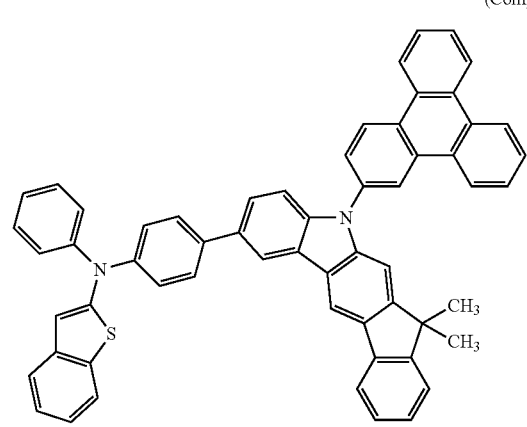
[Chemical Formula 51]
(Compound 45)
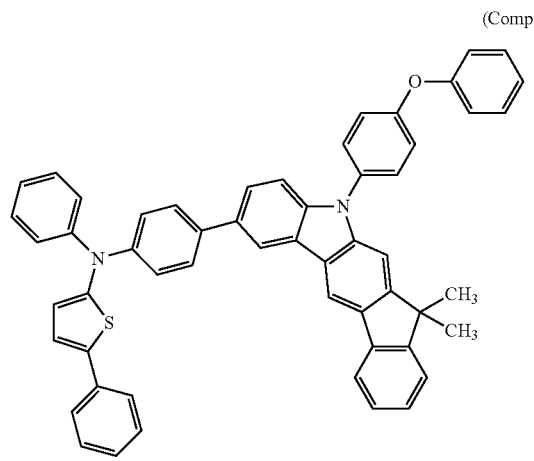
[Chemical Formula 52]
(Compound 46)
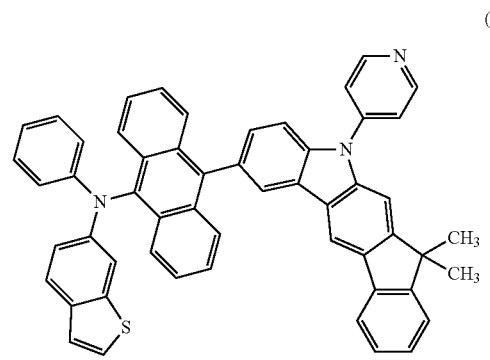

[Chemical Formula 53] (Compound 47)
[Chemical Formula 54] (Compound 48)
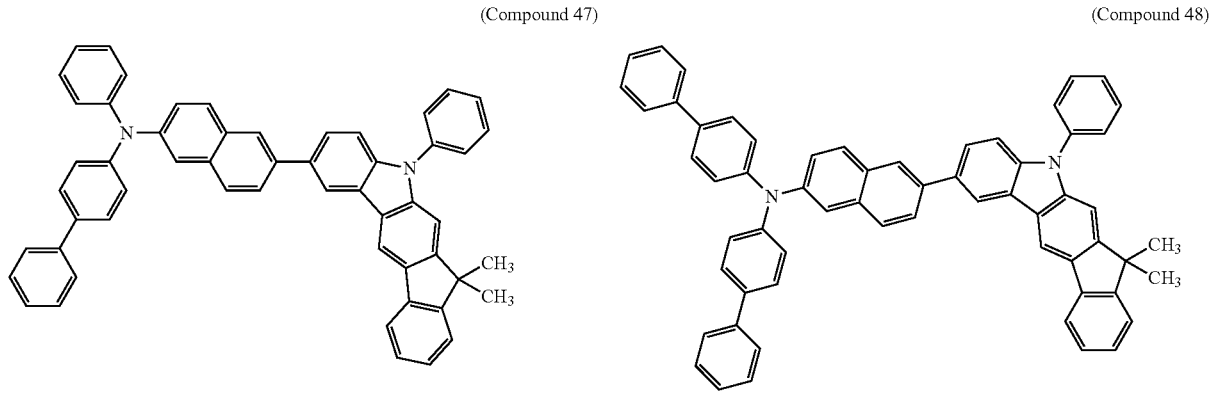
[Chemical Formula 55] (Compound 49)
[Chemical Formula 56] (Compound 50)
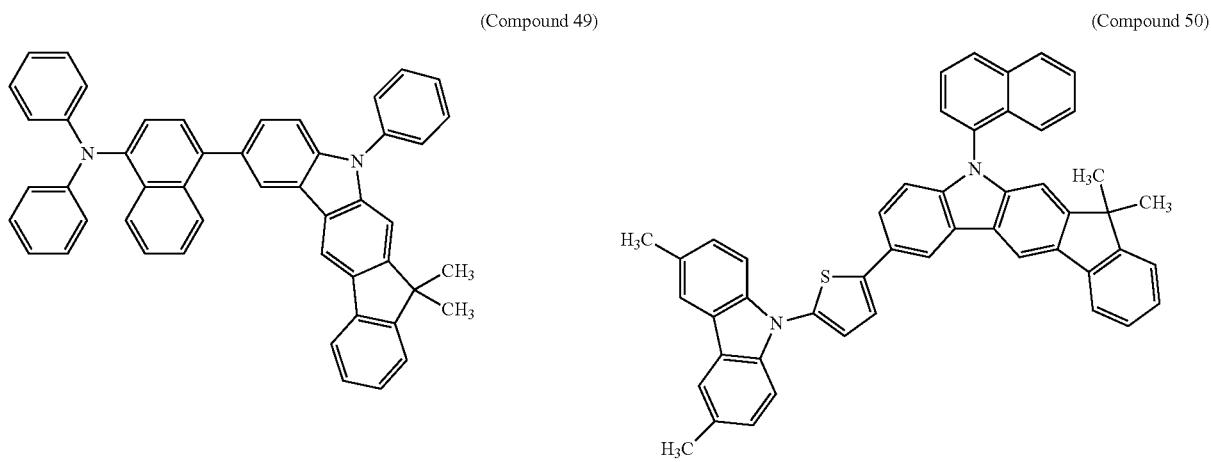
[Chemical Formula 57] (Compound 51)
[Chemical Formula 58] (Compound 52)
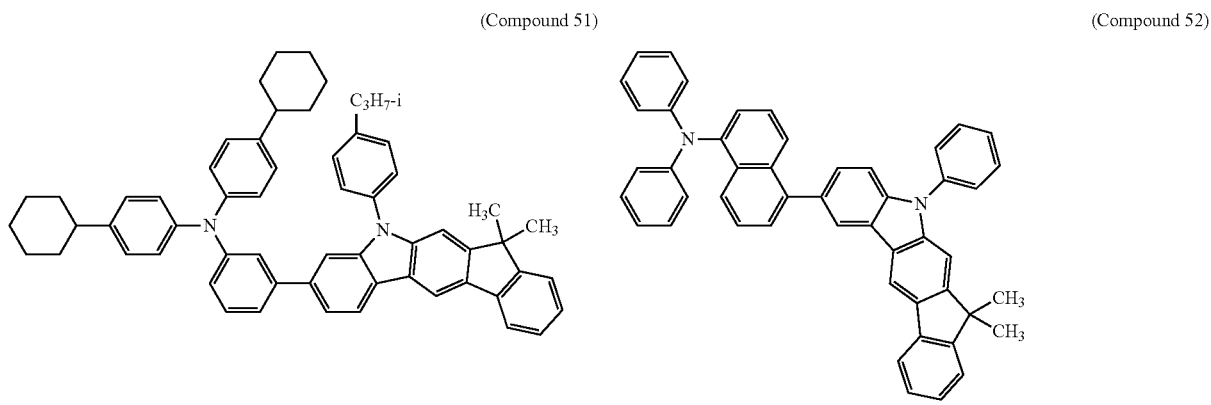

-continued
[Chemical Formula 59]
(Compound 53)
[Chemical Formula 60]
(Compound 54)
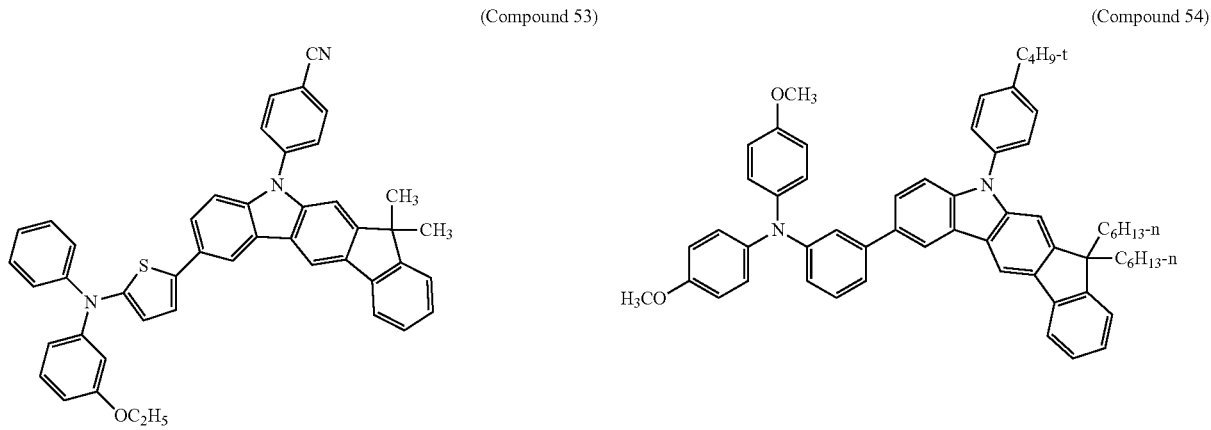
[Chemical Formula 61]
(Compound 55)
[Chemical Formula 62]
(Compound 56)
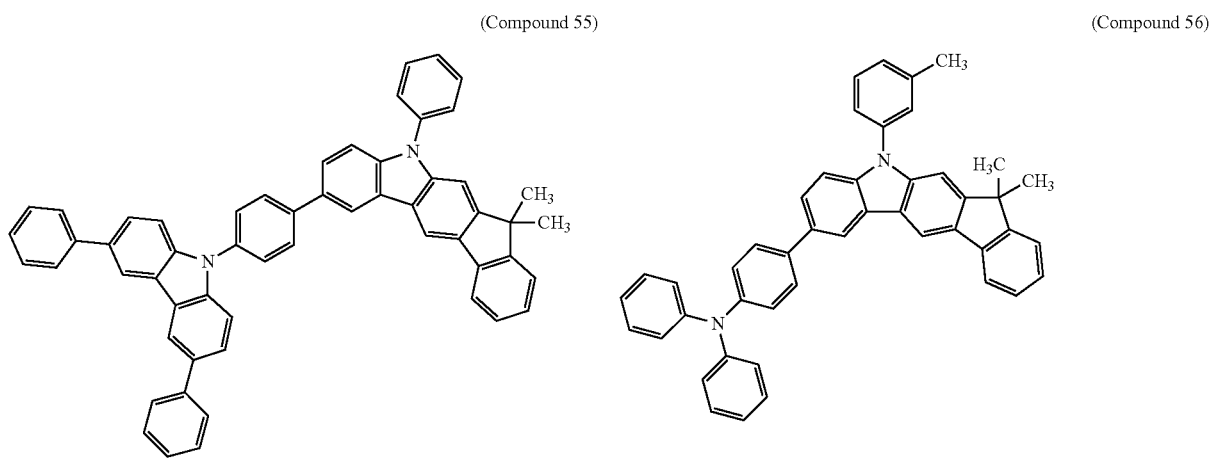
[Chemical Formula 63]
(Compound 57)
[Chemical Formula 64]
(Compound 58)
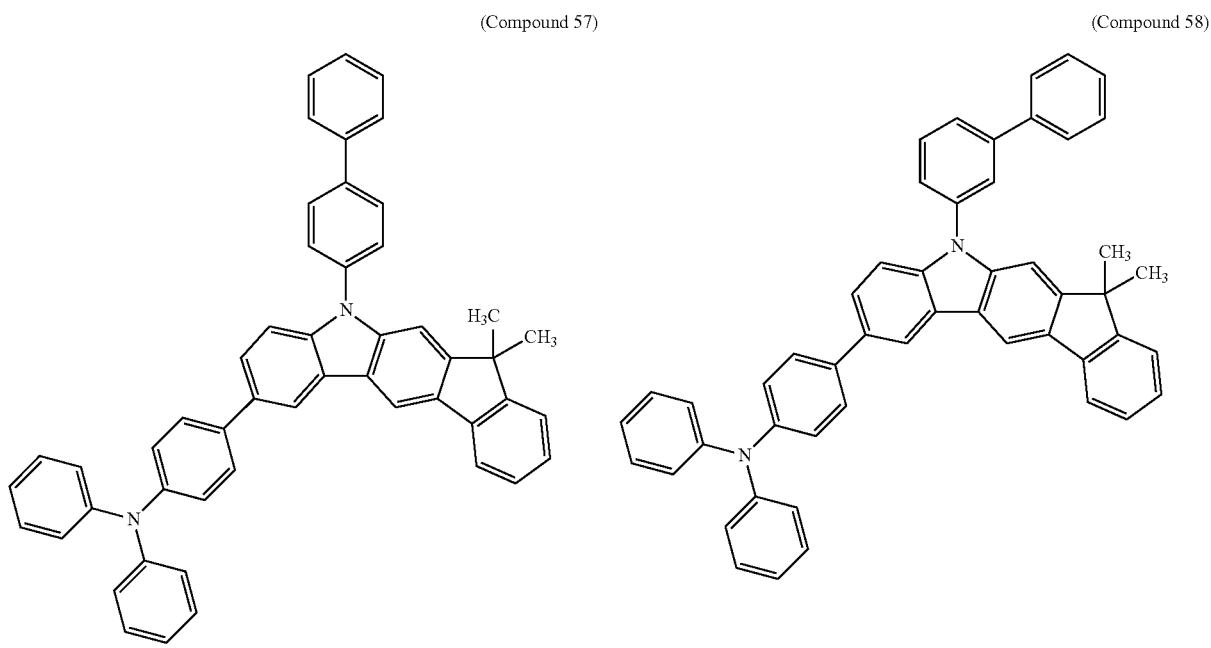

-continued
[Chemical Formula 65]
(Compound 59)
[Chemical Formula 66]
(Compound 60)
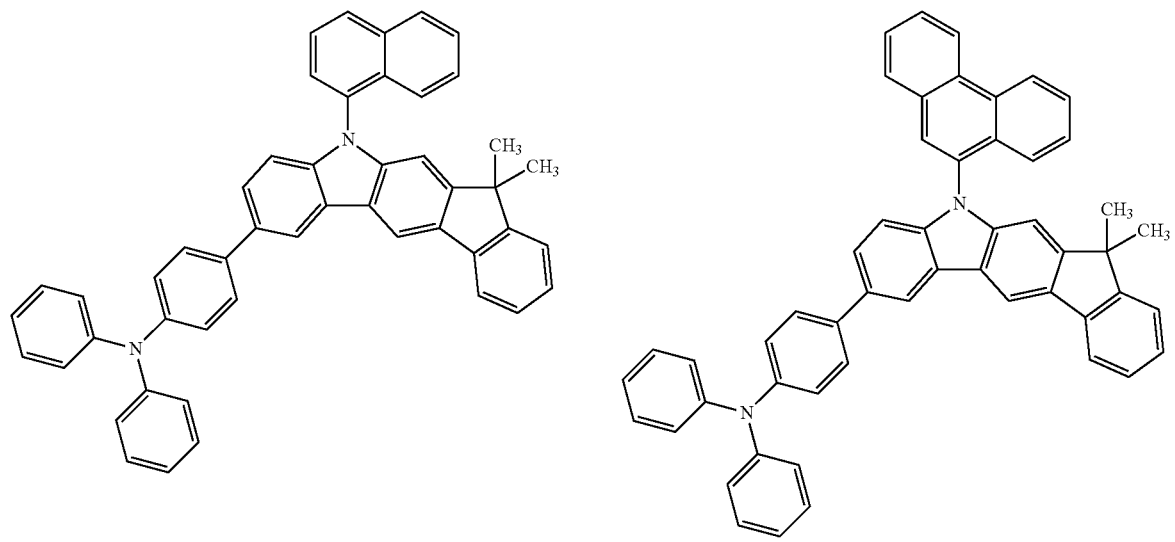
[Chemical Formula 67]
(Compound 61)
[Chemical Formula 68]
(Compound 62)
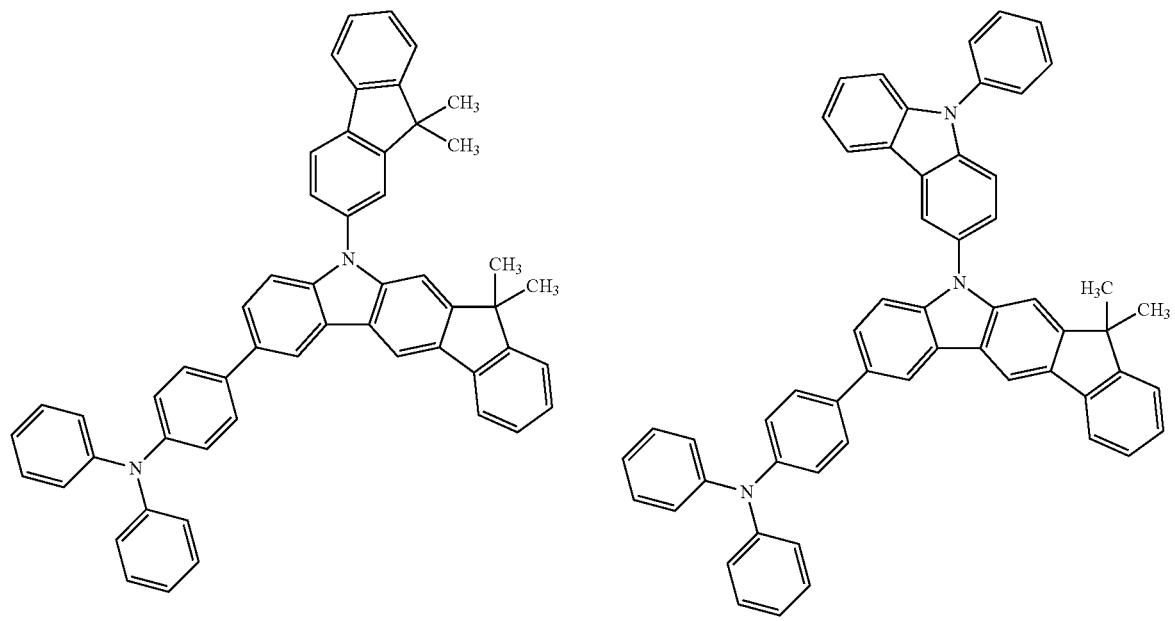

-continued
[Chemical Formula 69]
(Compound 63)
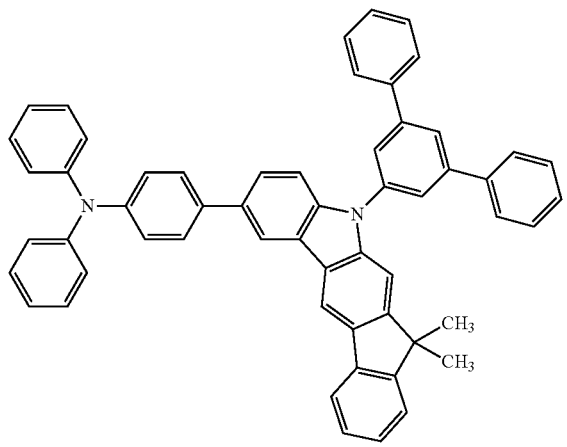
[Chemical Formula 70]
(Compound 64)
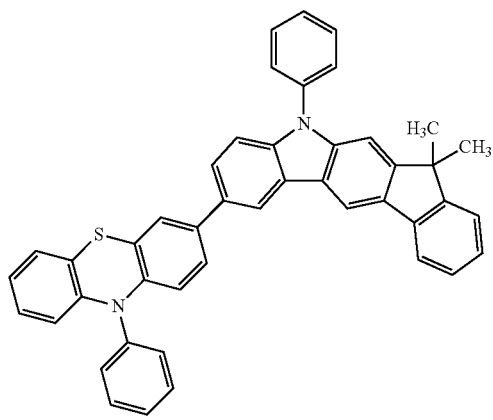
[Chemical Formula 71]
(Compound 65)
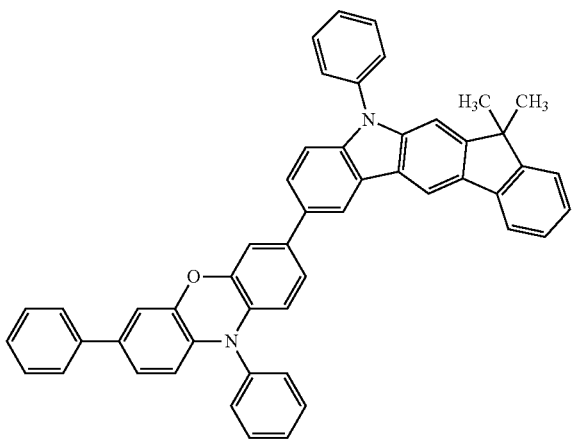
[Chemical Formula 72]
(Compound 66)
[Chemical Formula 73]
(Compound 67)
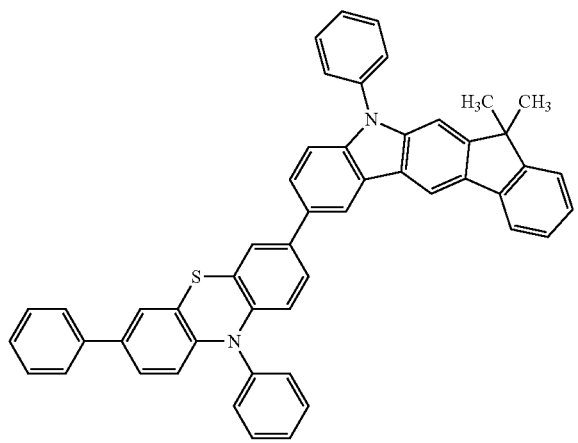
[Chemical Formula 74]
(Compound 68)
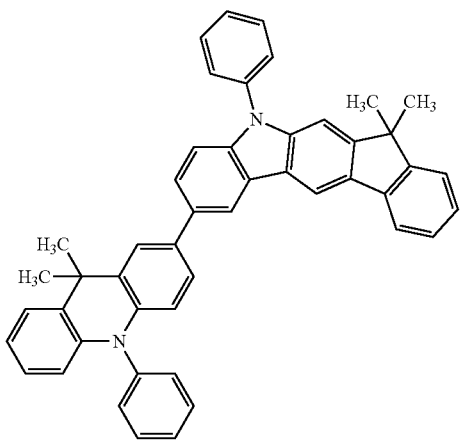

-continued
[Chemical Formula 75]
(Compound 69)
[Chemical Formula 76]
(Compound 70)
[Chemical Formula 77]
(Compound 71)
[Chemical Formula 78]
(Compound 72)
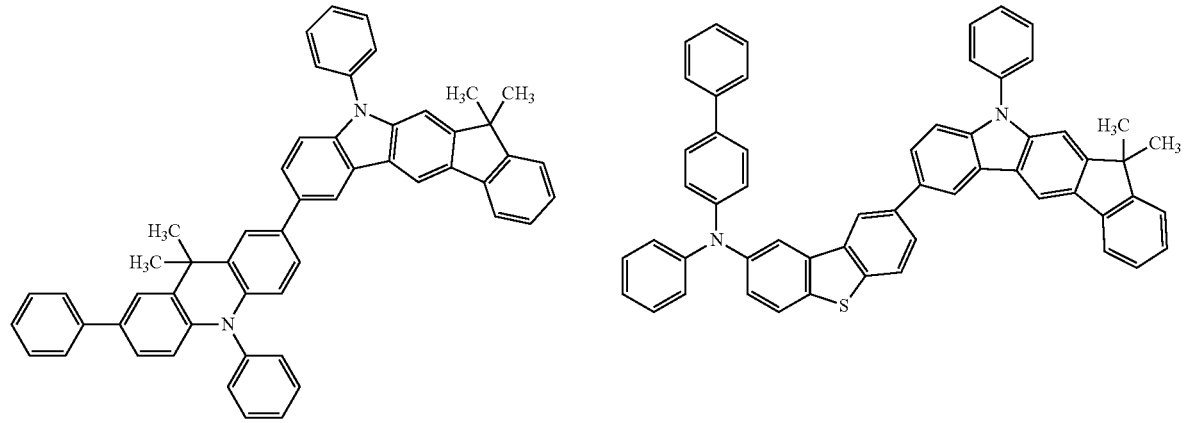
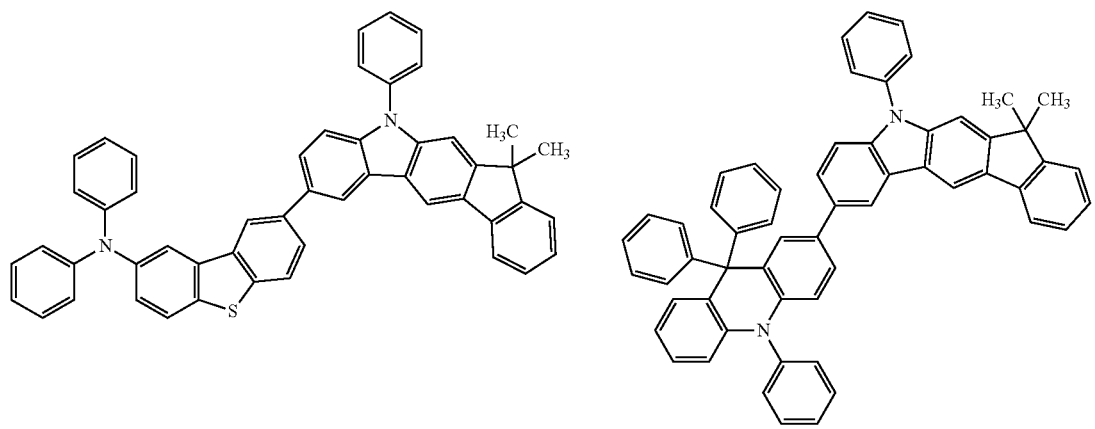
[Chemical Formula 79]
(Compound 73)
[Chemical Formula 80]
(Compound 74)
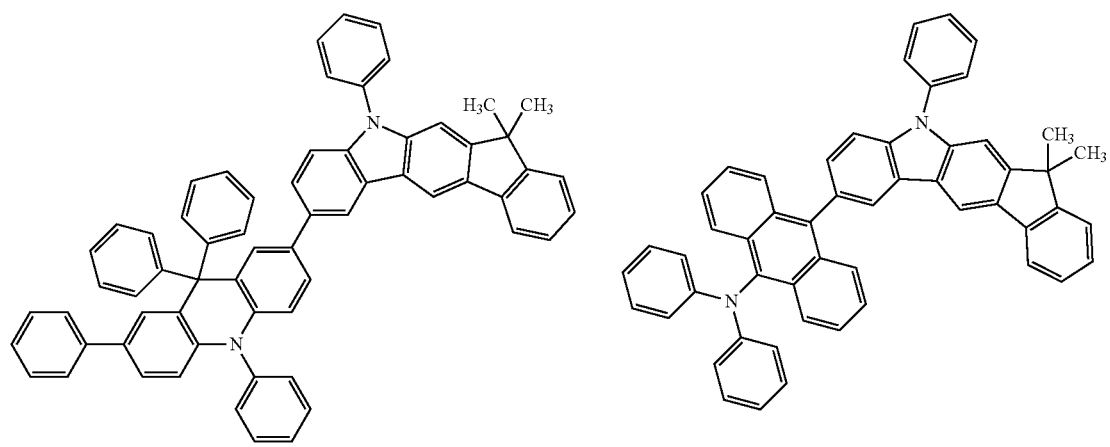

[Chemical Formula 81]
(Compound 75)
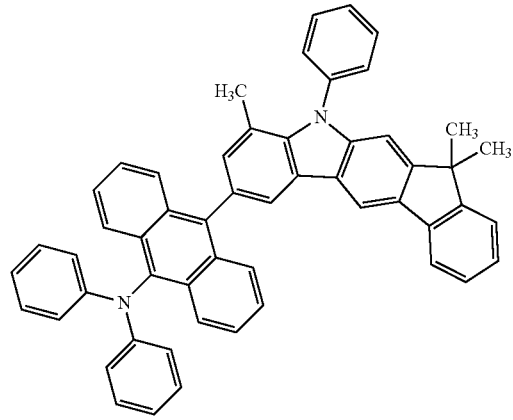
[Chemical Formula 82]
(Compound 76)
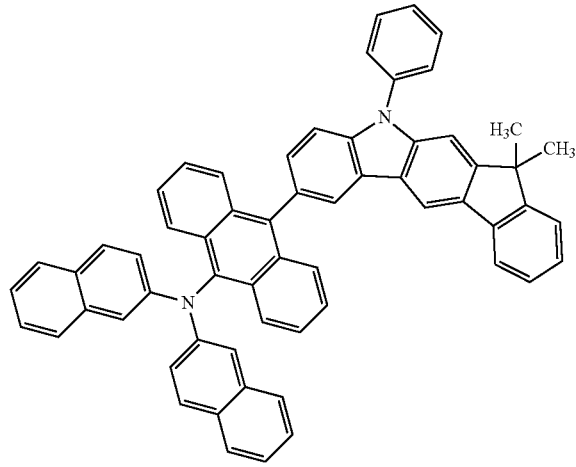
[Chemical Formula 83]
(Compound 77)
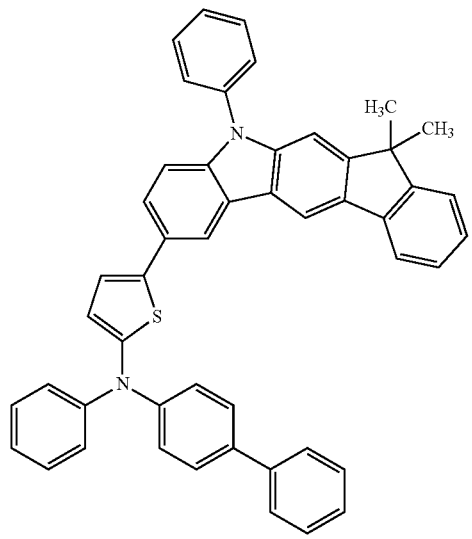
[Chemical Formula 84]
(Compound 78)
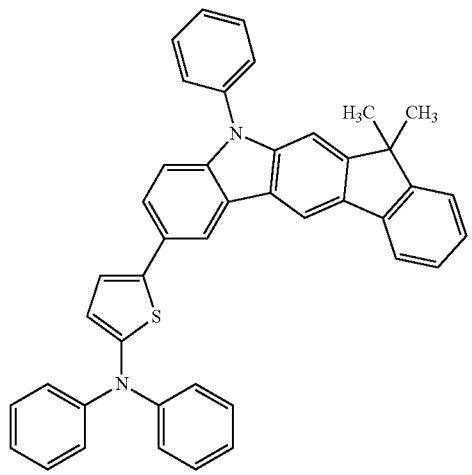
[Chemical Formula 85]
(Compound 79)
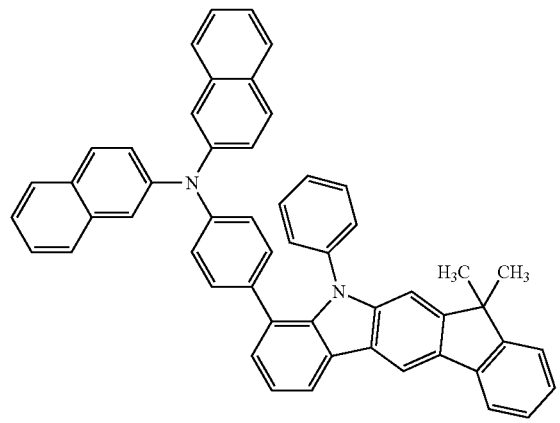
[Chemical Formula 86]
(Compound 80)
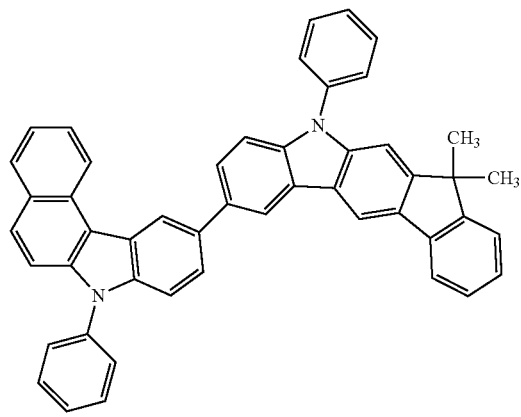

-continued
[Chemical Formula 87]
(Compound 81)
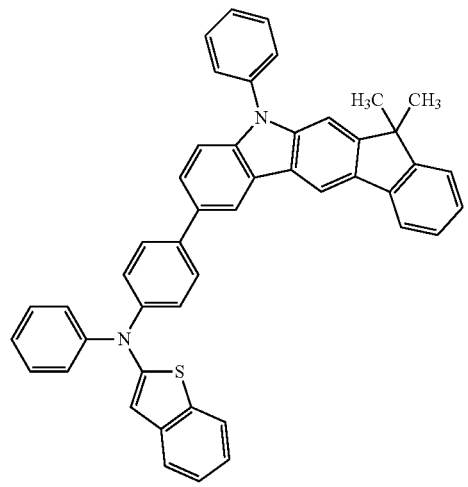
[Chemical Formula 88]
(Compound 82)
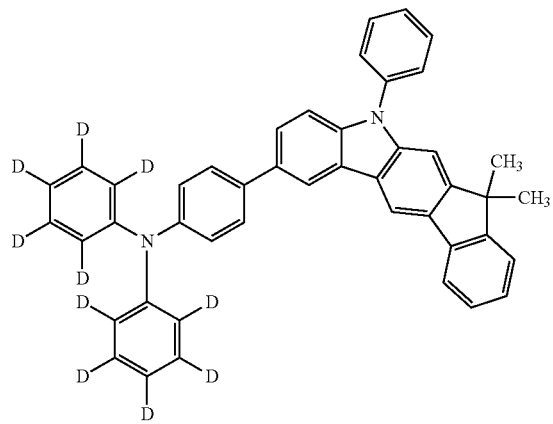
[Chemical Formula 89]
(Compound 83)
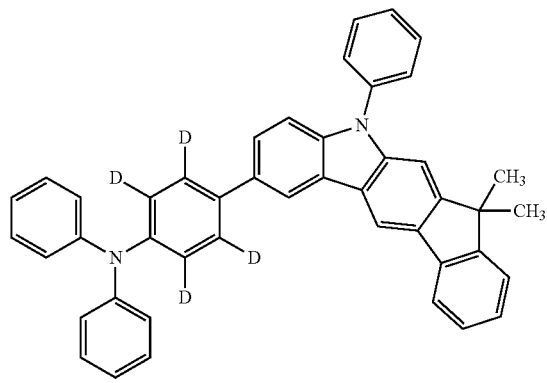
[Chemical Formula 90]
(Compound 84)
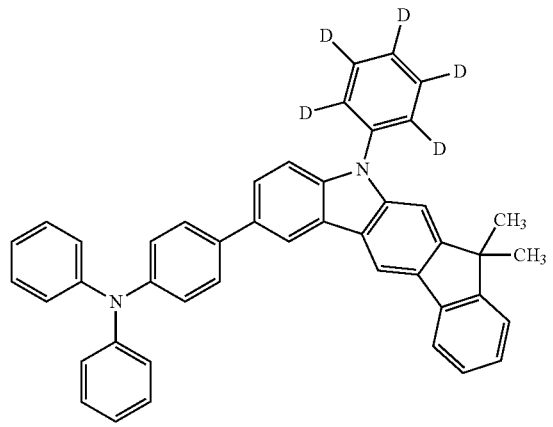
[Chemical Formula 91]
(Compound 85)
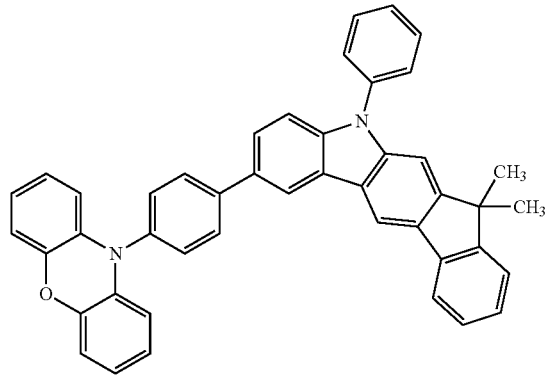
[Chemical Formula 92]
(Compound 86)
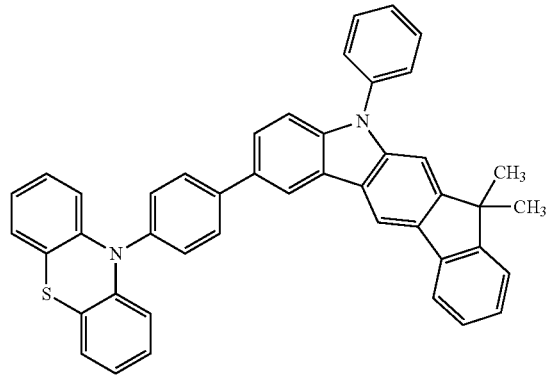

-continued
[Chemical Formula 93]
(Compound 87)
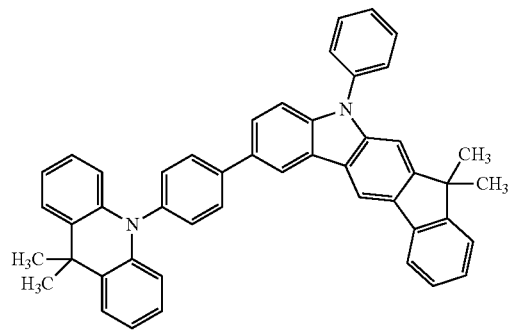
[Chemical Formula 94]
(Compound 88)
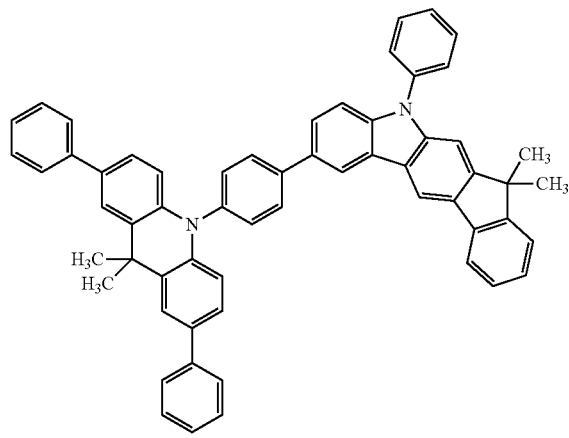
[Chemical Formula 95]
(Compound 89)
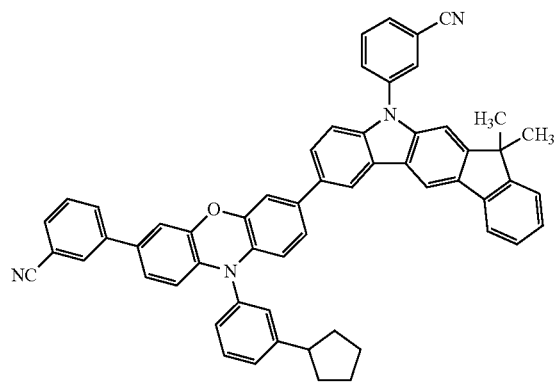
[Chemical Formula 96]
(Compound 90)
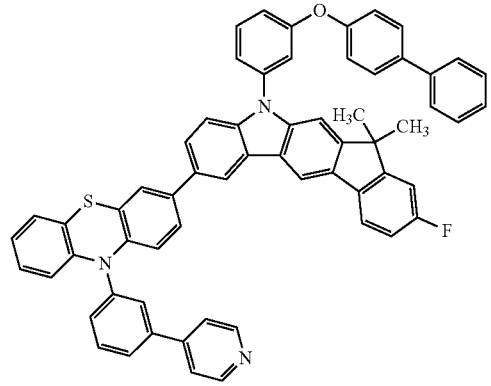
[Chemical Formula 97]
(Compound 91)
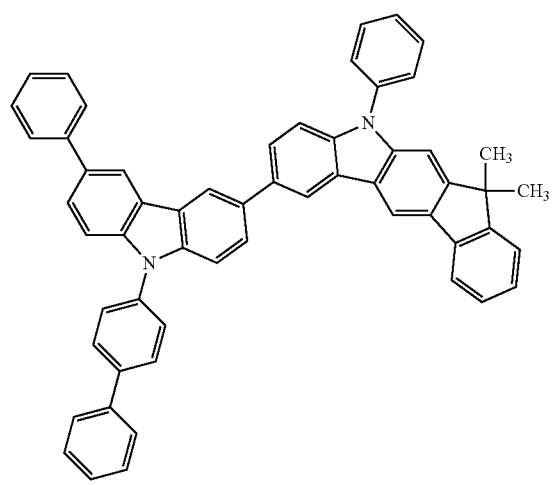
[Chemical Formula 98]
(Compound 92)
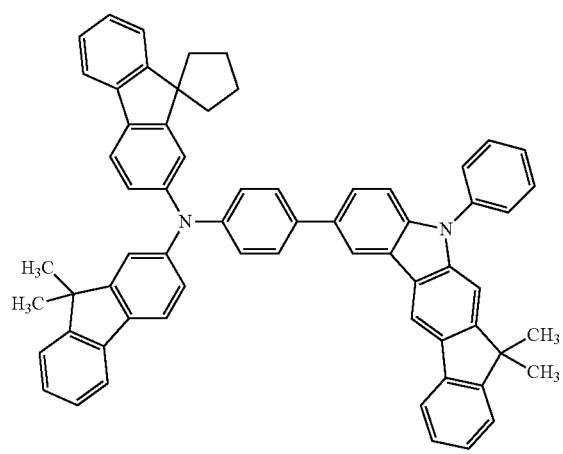

[Chemical Formula 99]
(Compound 93)
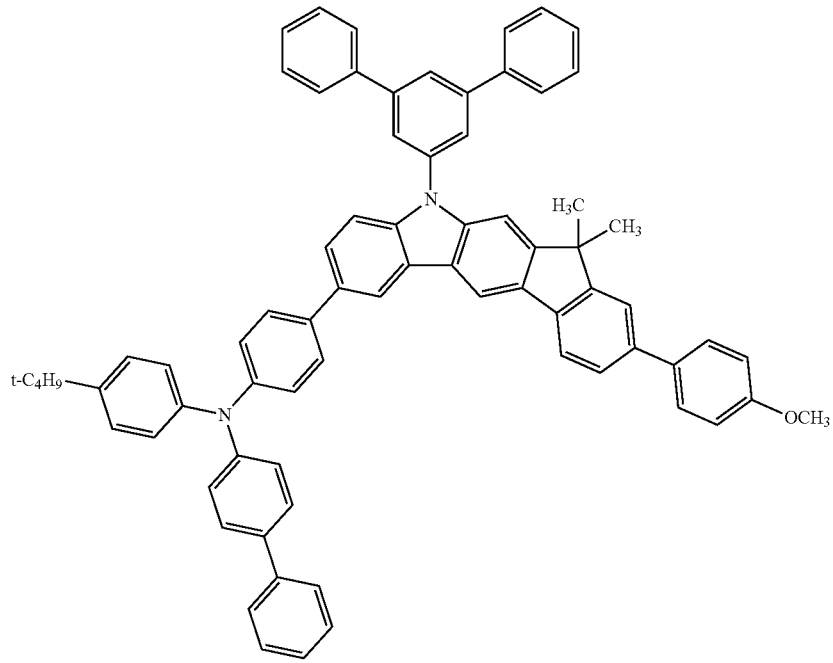
[Chemical Formula 100]
(Compound 94)
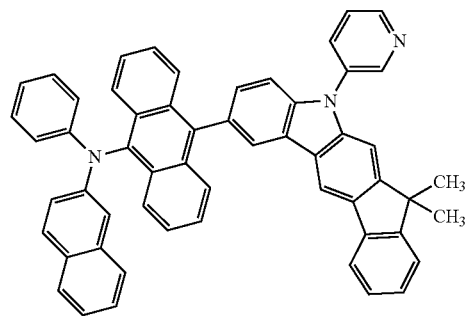
[Chemical Formula 101]
(Compound 95)
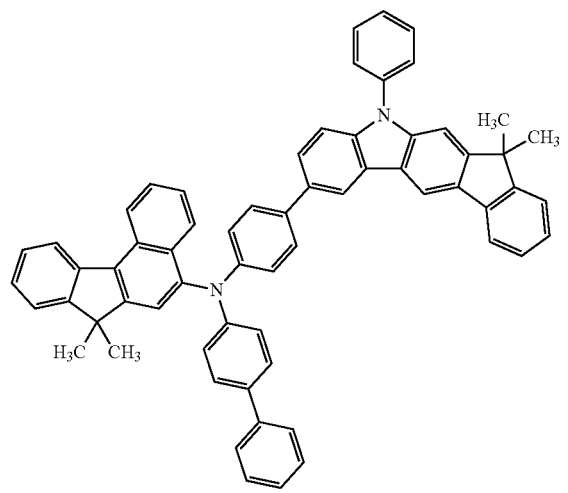

-continued
[Chemical Formula 102]
(Compound 96)
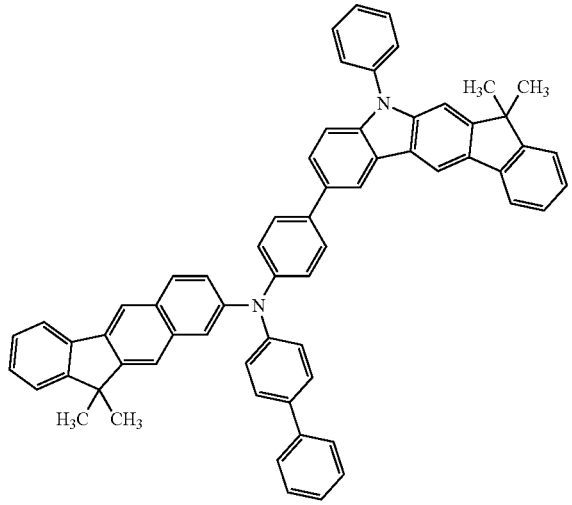
[Chemical Formula 103]
(Compound 97)
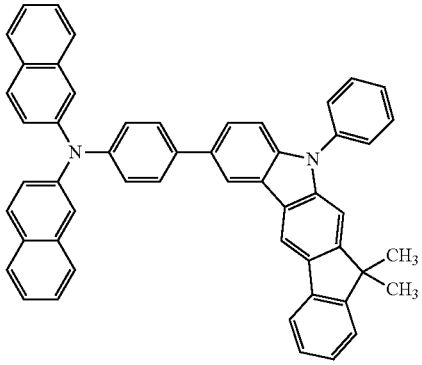
[Chemical Formula 104]
(Compound 98)
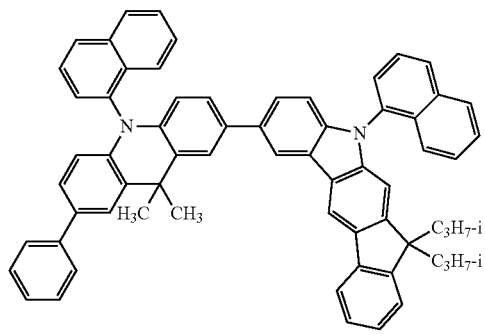
[Chemical Formula 105]
(Compound 99)
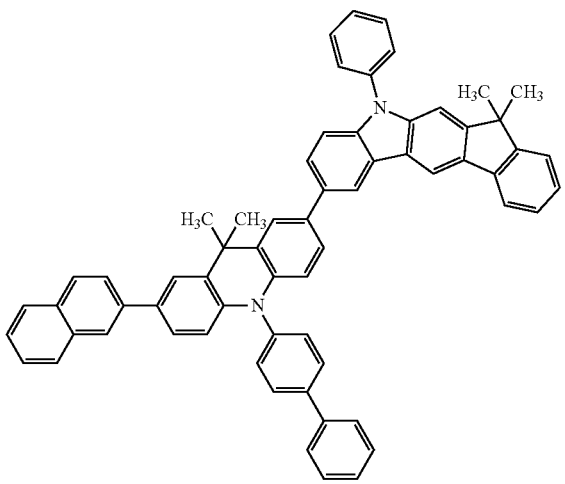
[Chemical Formula 106]
(Compound 100)
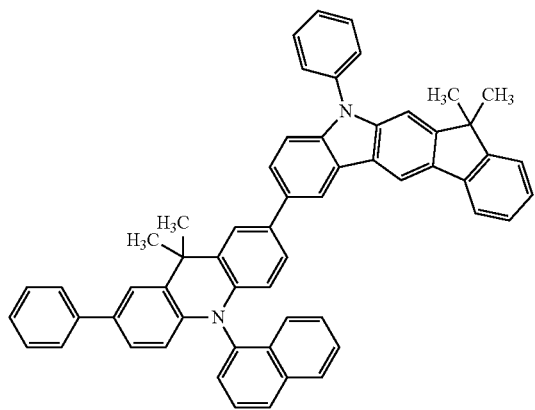
[Chemical Formula 107]
(Compound 101)
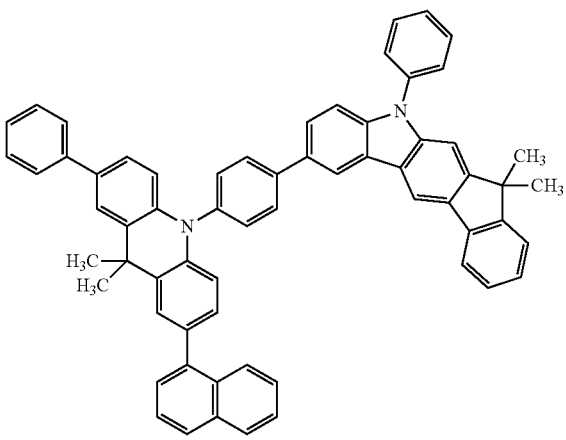

-continued
[Chemical Formula 108]
(Compound 102)
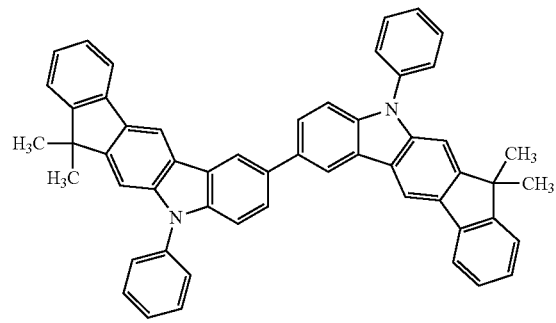
[Chemical Formula 109]
(Compound 103)
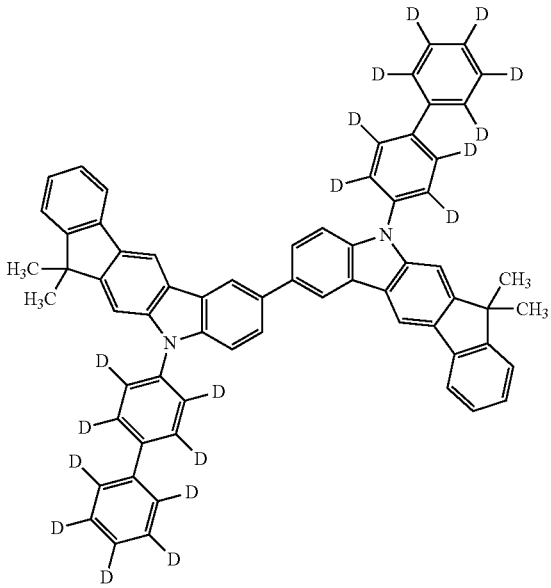
[Chemical Formula 110]
(Compound 104)
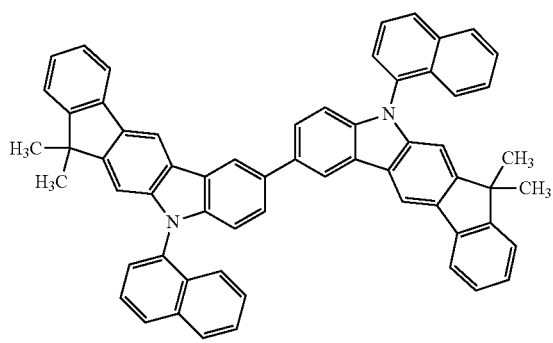
[Chemical Formula 111]
(Compound 105)
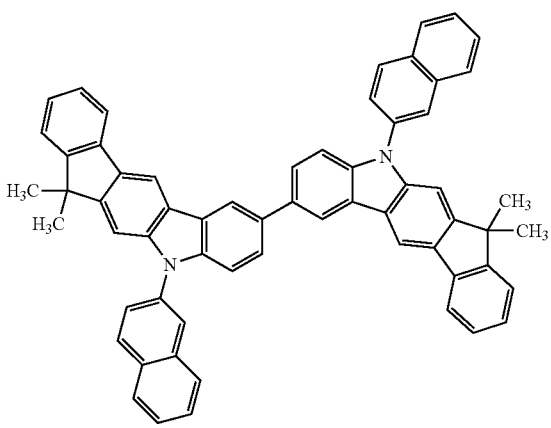

-continued
[Chemical Formula 112]
(Compound 106)
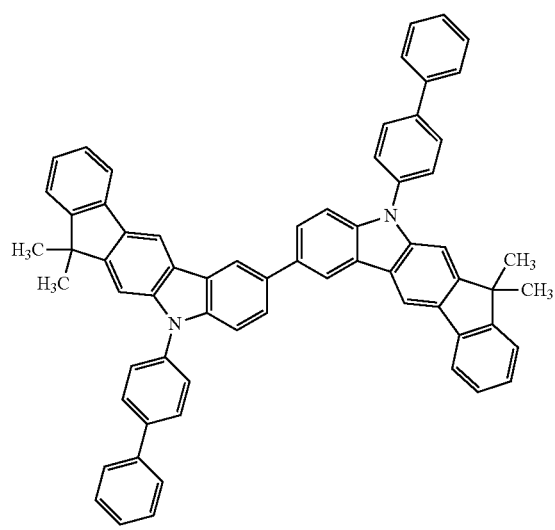
[Chemical Formula 113]
(Compound 107)
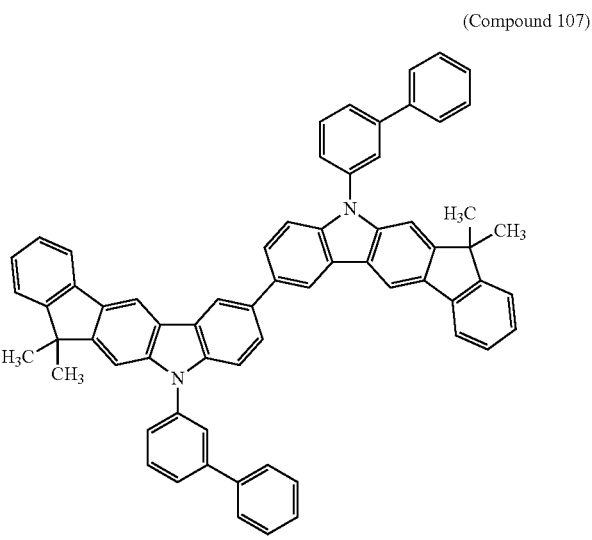
[Chemical Formula 114]
(Compound 108)
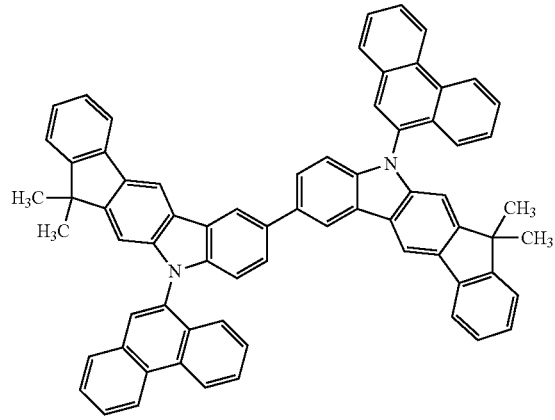
[Chemical Formula 115]
(Compound 109)
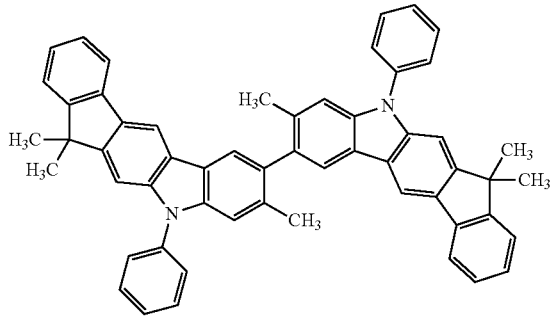
[Chemical Formula 116]
(Compound 110)
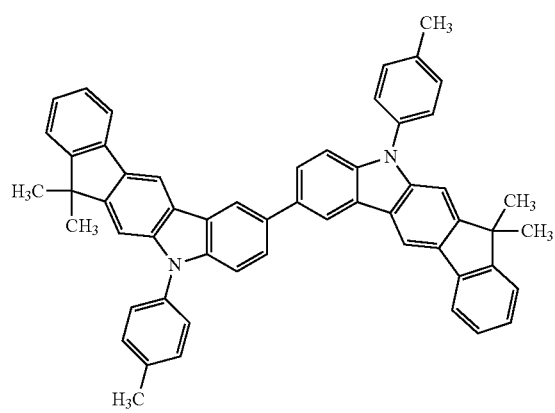
[Chemical Formula 117]
(Compound 111)
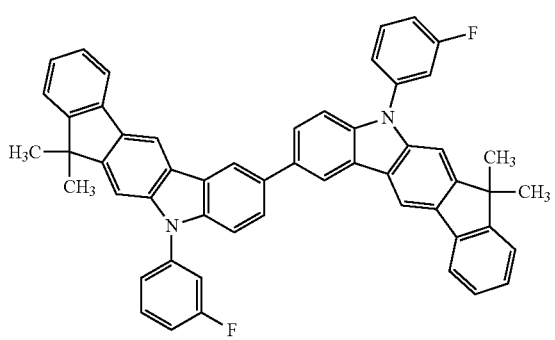

-continued
[Chemical Formula 118]
(Compound 112)
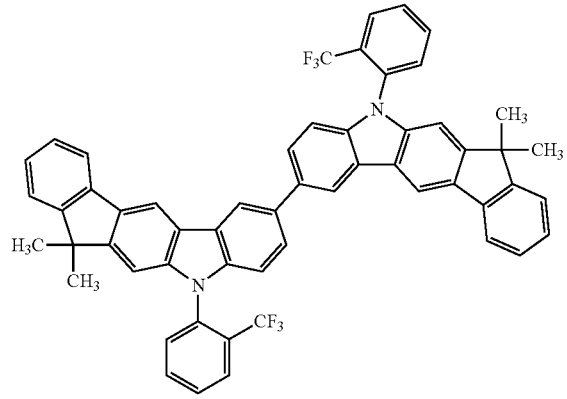
[Chemical Formula 119]
(Compound 113)
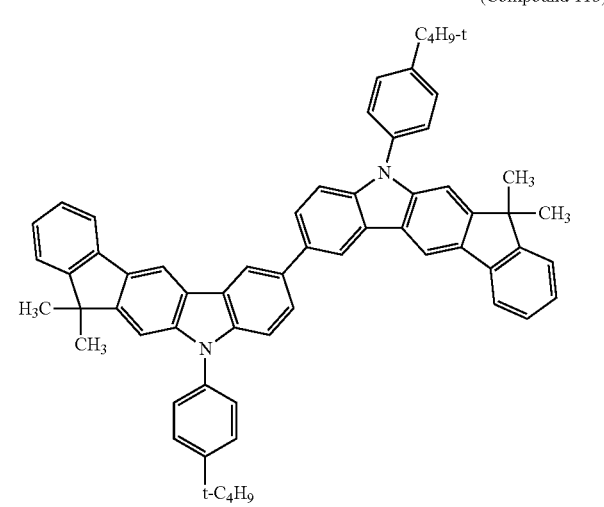
[Chemical Formula 120]
(Compound 114)
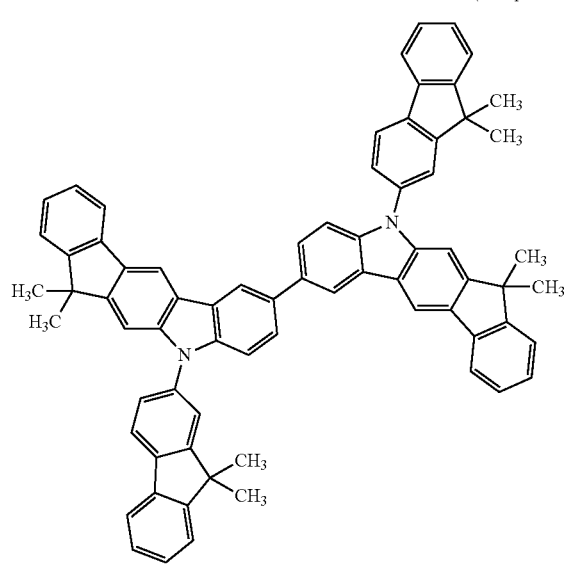
[Chemical Formula 121]
(Compound 115)
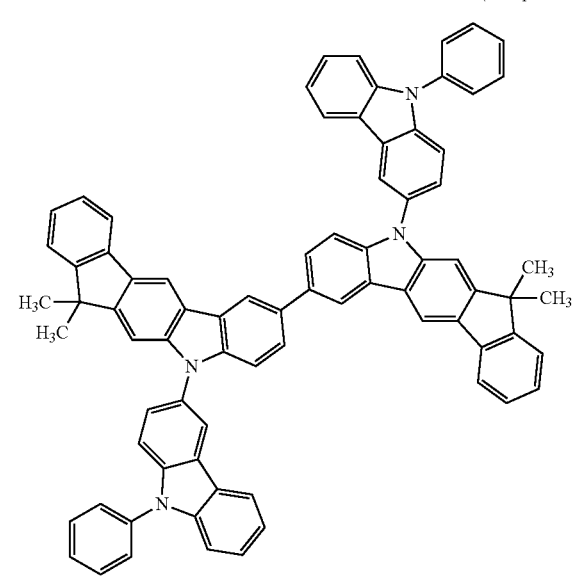
[Chemical Formula 122]
(Compound 116)
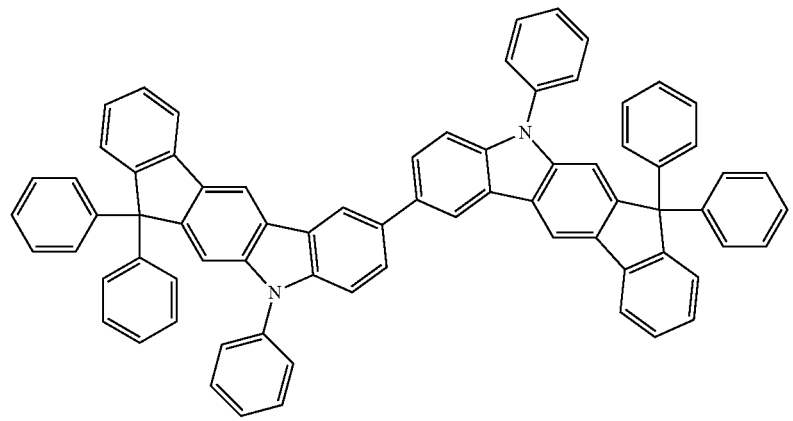

-continued
[Chemical Formula 123]
(Compound 117)
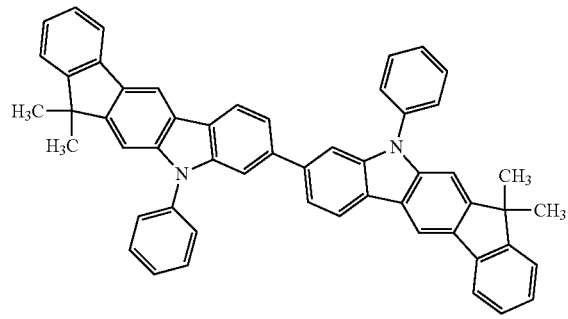
[Chemical Formula 124]
(Compound 118)
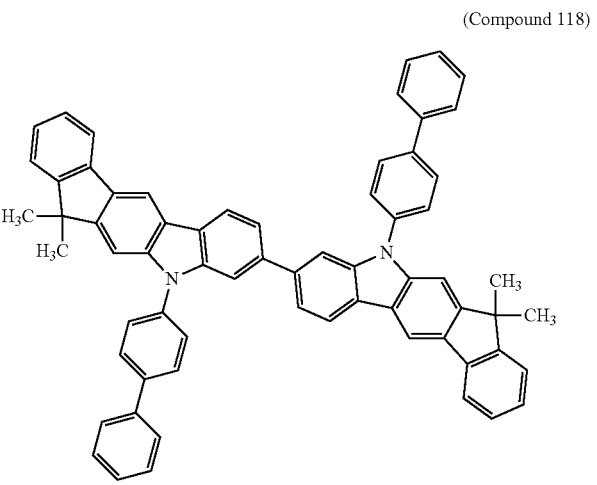
[Chemical Formula 125]
(Compound 119)
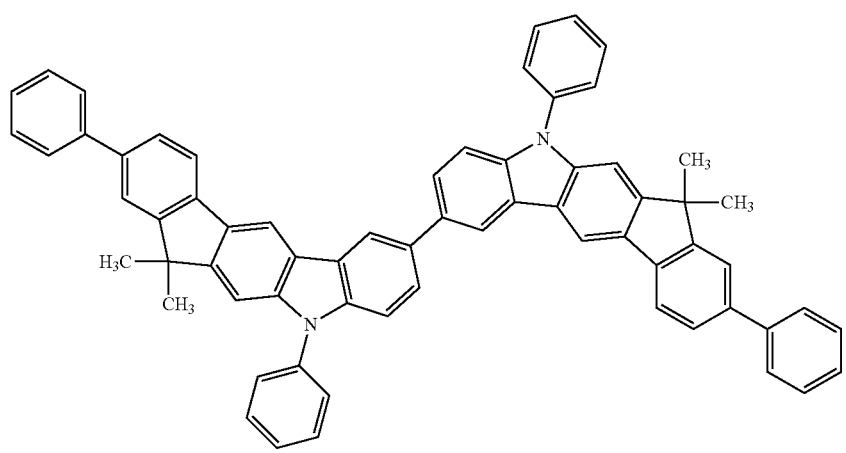
[Chemical Formula 126]
(Compound 120)
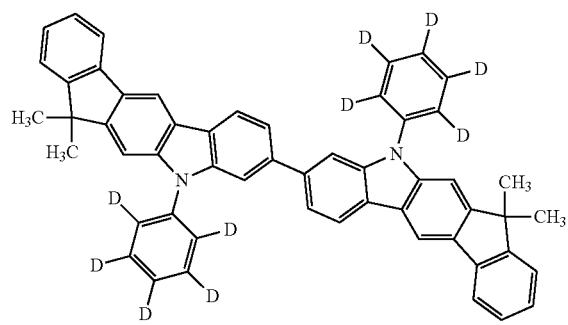
[Chemical Formula 127]
(Compound 121)
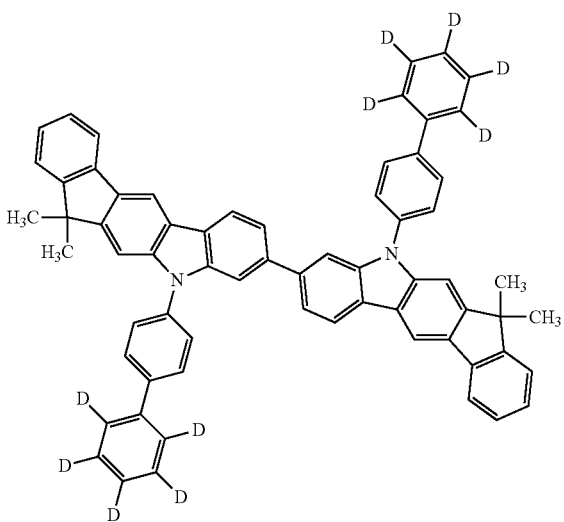

[Chemical Formula 128]

(Compound 122)

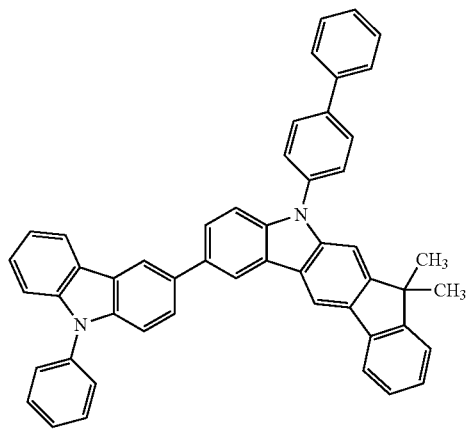

[Chemical Formula 129]

(Compound 123)

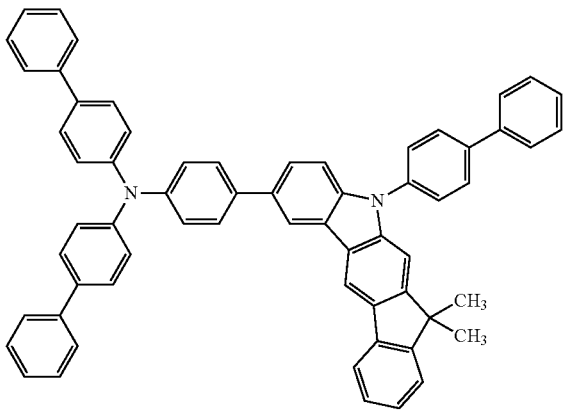

[Chemical Formula 130]

(Compound 124)

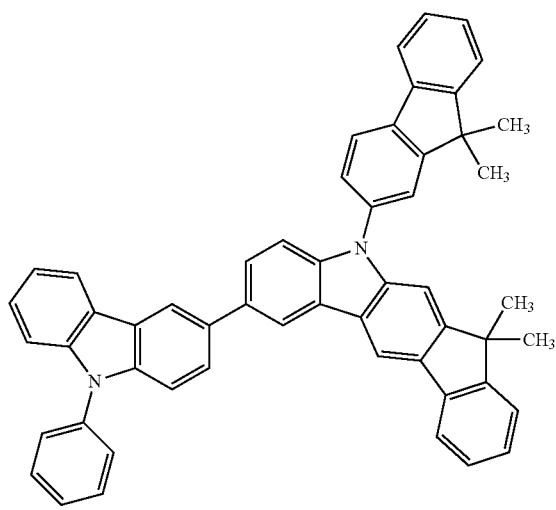

These compounds were purified by methods such as column chromatography, adsorption using, for example, silica gel, activated carbon, or activated clay, and recrystallization or crystallization using a solvent. The compounds were identified by an NMR analysis. A glass transition point (Tg) and a work function were measured as material property values. The glass transition point (Tg) can be used as an index of stability in the thin-film state, and the work function can be used as an index of hole transportability.

The glass transition point (Tg) was measured by a high-sensitive differential scanning calorimeter (DSC3100S produced by Bruker AXS) using powder.

For the measurement of the work function, a 100 nm-thick thin film was fabricated on an ITO substrate, and an atmosphere photoelectron spectrometer (AC-3 produced by Riken Keiki Co., Ltd.) was used.

The organic EL device of the present invention may have a structure including an anode, a hole transport layer, an electron blocking layer, a light emitting layer, an electron transport layer, and a cathode successively formed on a substrate, optionally with a hole injection layer between the anode and the hole transport layer, or with an electron injection layer between the electron transport layer and the cathode. In such multilayer structures, some of the organic layers may be omitted. For example, the device may be configured to include an anode, a hole transport layer, a light emitting layer, an electron transport layer, and a cathode successively formed on a substrate.

Electrode materials with high work functions such as ITO and gold are used as the anode of the organic EL device of the present invention. The hole injection layer of the organic EL device of the present invention may be made of material such as porphyrin compounds as represented by copper phthalocyanine, starburst-type triphenylamine derivatives, various triphenylamine tetramers, accepting heterocyclic compounds such as hexacyano azatriphenylene, and coating-type polymer materials, in addition to the compounds of general formula (1) having an indenocarbazole ring structure of the present invention. These materials may be formed into a thin film by a vapor deposition method or other known methods such as a spin coating method and an inkjet method.

Examples of material used for the hole transport layer of the organic EL device of the present invention can be benzidine derivatives such as N,N'-diphenyl-N,N'-di(m-tolyl)benzidine (hereinafter referred to as TPD), N,N'-diphenyl-N,N'-di(α-naphthyl)benzidine (hereinafter referred to as NPD), and N,N,N',N'-tetrabiphenylylbenzidine; 1,1-bis[4-(di-4-tolylamino)phenyl]cyclohexane (hereinafter referred to as TAPC); and various triphenylamine trimers and tetramers, in addition to the compounds of general formula (1) having an indenocarbazole ring structure of the present invention. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. Examples of material used for the hole injection/transport layer can be coating-type polymer materials such as poly(3,4-ethylenedioxythiophene) (hereinafter referred to as PEDOT)/poly(styrene sulfonate) (hereinafter referred to as PSS). These materials may be formed into a thin-film by a vapor deposition method or other known methods such as a spin coating method and an inkjet method.

Further, material used for the hole injection layer or the hole transport layer may be obtained by p-doping trisbromophenylamine hexachloroantimony or the like into the material commonly used for these layers, or may be, for example, polymer compounds each having a TPD structure as a part of the compound structure.

Examples of material used for the electron blocking layer of the organic EL device of the present invention can be compounds having an electron blocking effect, including, for example, carbazole derivatives such as 4,4',4''-tri(N-carbazolyl)triphenylamine (hereinafter referred to as TCTA), 9,9-bis[4-(carbazol-9-yl)phenyl]fluorene, 1,3-bis(carbazol-9-yl)benzene (hereinafter referred to as mCP), and 2,2-bis(4-carbazol-9-ylphenyl)adamantane (hereinafter referred to as Ad-Cz); and compounds having a triphenylsilyl group and a triarylamine structure, as represented by 9-[4-(carbazol-9-yl)phenyl]-9-[4-(triphenylsilyl)phenyl]-9H-fluorene, in addition to the compounds of general formula (1) having an indenocarbazole ring structure of the present invention. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the light emitting layer of the organic EL device of the present invention can be various metal complexes, anthracene derivatives, bis(styryl)benzene derivatives, pyrene derivatives, oxazole derivatives, and polyparaphenylene vinylene derivatives, in addition to quinolinol derivative metal complexes such as $Alq_3$. Further, the light emitting layer may comprise a host material and a dopant material. Examples of the host material can be thiazole derivatives, benzimidazole derivatives, and polydialkyl fluorene derivatives, in addition to the above light-emitting materials and the compounds of general formula (1) having an indenocarbazole ring structure of the present invention. Examples of the dopant material can be quinacridone, coumarin, rubrene, perylene, derivatives thereof, benzopyran derivatives, rhodamine derivatives, and aminostyryl derivatives. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer.

Further, the light-emitting material may be a phosphorescent light-emitting material. Phosphorescent materials as metal complexes of metals such as iridium and platinum may be used as the phosphorescent light-emitting material. Examples of the phosphorescent materials can be green phosphorescent materials such as $Ir(ppy)_3$, blue phosphorescent materials such as FIrpic and $FIr_6$, and red phosphorescent materials such as $Btp_2Ir(acac)$. As the hole injecting and transporting host material, the compounds of general formula (1) having an indenocarbazole ring structure of the present invention may be used in addition to carbazole derivatives such as 4,4'-di(N-carbazolyl)biphenyl (hereinafter referred to as CBP), TCTA, and mCP. Compounds such as p-bis(triphenylsilyl)benzene (hereinafter referred to as UGH2) and 2,2',2''-(1,3,5-phenylene)-tris(1-phenyl-1H-benzimidazole) (hereinafter referred to as TPBI) may be used as the electron transporting host material to produce a high-performance organic electroluminescent device.

In order to avoid concentration quenching, it is preferable to dope the host material with the phosphorescent light-emitting material by co-evaporation in a range of 1 to 30 weight percent to the whole light emitting layer.

These materials may be formed into a thin-film by using a vapor deposition method or other known methods such as a spin coating method and an inkjet method.

The hole blocking layer of the organic EL device of the present invention may be formed by using hole blocking compounds such as various rare earth complexes, triazole derivatives, triazine derivatives, and oxadiazole derivatives, in addition to the metal complexes of phenanthroline derivatives such as bathocuproin (hereinafter referred to as BCP), and the metal complexes of quinolinol derivatives such as aluminum(III) bis(2-methyl-8-quinolinate)-4-phenylphenolate (hereinafter referred to as BAlq). These materials may also serve as the material of the electron transport layer. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the electron transport layer of the organic EL device of the present invention can be various metal complexes, triazole derivatives, triazine derivatives, oxadiazole derivatives, thiadiazole derivatives, carbodiimide derivatives, quinoxaline derivatives, phenanthroline derivatives, and silole derivatives, in addition to the metal complexes of quinolinol derivatives such as $Alq_3$ and BAlq. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the electron injection layer of the organic EL device of the present invention can be alkali metal salts such as lithium fluoride and cesium fluoride; alkaline earth metal salts such as magnesium fluoride; and metal oxides such as aluminum oxide. However, the electron injection layer may be omitted in the preferred selection of the electron transport layer and the cathode.

The cathode of the organic EL device of the present invention may be made of an electrode material with a low work function such as aluminum, or an alloy of an electrode material with an even lower work function such as a magnesium-silver alloy, a magnesium-indium alloy, or an aluminum-magnesium alloy.

The following describes an embodiment of the present invention in more detail based on Examples. The present invention, however, is not restricted to the following Examples.

Example 1

Synthesis of 12,12-dimethyl-10-phenyl-7-(9-phenyl-9H-carbazol-3-yl)-10,12-dihydroindeno[2,1-b]carbazole (Compound 5)

N-(9,9-dimethyl-9H-fluorene-2-yl)-2-bromo-aniline (18.5 g), potassium acetate (6.98 g), and DMF (95 ml) were added to a nitrogen-substituted reaction vessel and aerated with nitrogen gas for 1 hour. The mixture was heated after adding tetrakis(triphenylphosphine)palladium (1.18 g) and stirred at 100° C. for 11 hours. After the mixture was cooled to a room temperature, the reaction liquid was added to water (300 ml) and extraction was performed with toluene (300 ml). An organic layer obtained was washed with water (200 ml) twice, dehydrated with anhydrous magnesium sulfate, and concentrated under reduced pressure to obtain a crude product. The crude product was purified by column chromatography (carrier: silica gel; eluent: toluene/n-hexane) to obtain a pale yellow powder of 12,12-dimethyl-10,12-dihydroindeno[2,1-b]carbazole (7.9 g; yield 55.2%).

The resulting 12,12-dimethyl-10,12-dihydroindeno[2,1-b]carbazole (7.8 g), iodobenzene (3.7 ml), sodium bisulfite (0.43 g), a copper powder (0.17 g), 3,5-di(tert-butyl)salicylic acid (0.69 g), potassium carbonate (5.71 g), and dodecylbenzene (10 ml) were added to a nitrogen-substituted reaction vessel, heated, and stirred at 170° C. for 10 hours. The mixture was cooled to 100° C., extracted by adding toluene (100 ml), concentrated under reduced pressure, and crystallized using n-hexane (30 ml) to obtain a pale yellow powder of 12,12-dimethyl-10-phenyl-10,12-dihydroindeno[2,1-b]carbazole (8.73 g; yield 88.3%).

The resulting 12,12-dimethyl-10-phenyl-10,12-dihydroindeno[2,1-b]carbazole (7.5 g) and DMF (53 ml) were added to a reaction vessel. N-bromosuccinimide (3.72 g) was added under ice-cooled conditions, and the mixture was stirred for 9 hours and then left for one night. Water (260 ml) was added, and the mixture was subjected to filtration to obtain a brownish white powder of 7-bromo-12,12-dimethyl-10-phenyl-10,12-dihydroindeno[2,1-b]carbazole (8.67 g; yield 94.6%).

The resulting 7-bromo-12,12-dimethyl-10-phenyl-10,12-dihydroindeno[2,1-b]carbazole (2.0 g), 9-phenyl-3-(4,4,5,5-tetramethyl-1,3,2-dioxaborolan-2-yl)-9H-carbazole (1.68 g), a toluene/ethanol (4/1, v/v) mixed solvent (15 ml), and a 2M potassium carbonate aqueous solution (3.4 ml) were added to a nitrogen-substituted reaction vessel and aerated with nitrogen gas for 30 min under ultrasonic irradiation. The mixture was heated after adding tetrakis(triphenylphosphine)palladium (0.26 g), and stirred at 73° C. for 5 hours. After the mixture was cooled to a room temperature, toluene (30 ml) and water (20 ml) were added to perform liquid separation in order to collect an organic layer. The organic layer was washed with saturated brine, dehydrated with anhydrous magnesium sulfate, and concentrated under reduced pressure to obtain a crude product. The crude product was purified by column chromatography (carrier: silica gel; eluent: toluene/n-hexane) to obtain a white powder of 12,12-dimethyl-10-phenyl-7-(9-phenyl-9H-carbazol-3-yl)-10,12-dihydroindeno[2,1-b]carbazole (1.5 g; yield 54.7%).

The structure of the resulting white powder was identified by NMR. The $^1$H-NMR measurement result is presented in FIG. 1.

$^1$H-NMR (THF-$d_8$) detected 32 hydrogen signals, as follows. δ (ppm)=8.66 (1H), 8.64 (1H), 8.59 (1H), 8.23-8.29 (1H), 7.88-7.90 (1H), 7.83-7.85 (1H), 7.78-7.80 (1H), 7.66-7.71 (8H), 7.42-7.53 (7H), 7.37-7.40 (1H), 7.31-7.33 (1H), 7.26-7.29 (1H), 7.21-7.24 (1H), 1.51 (6H).

Example 2

Synthesis of 12,12-dimethyl-10-phenyl-7-(4-diphenylamino-phenyl)-10,12-dihydroindeno[2,1-b]carbazole (Compound 6)

7-Bromo-12,12-dimethyl-10-phenyl-10,12-dihydroindeno[2,1-b]carbazole synthesized in Example 1 (2.0 g), 4-diphenylamino-phenylboronic acid (1.32 g), a toluene/ethanol (4/1, v/v) mixed solvent (15 ml), and a 2M potassium carbonate aqueous solution (3.4 ml) were added to a nitrogen-substituted reaction vessel and aerated with nitrogen gas for 30 min under ultrasonic irradiation. The mixture was heated after adding tetrakis(triphenylphosphine)palladium (0.26 g), and stirred at 73° C. for 5 hours. After the mixture was cooled to a room temperature, toluene (30 ml) and water (20 ml) were added to perform liquid separation in order to collect an organic layer. The organic layer was washed with saturated brine, dehydrated with anhydrous magnesium sulfate, and concentrated under reduced pressure to obtain a crude product. The crude product was purified by column chromatography (carrier: silica gel; eluent: toluene/n-hexane) to obtain a pale yellowish white powder of 12,12-dimethyl-10-phenyl-7-(4-diphenylamino-phenyl)-10,12-dihydroindeno[2,1-b]carbazole (1.6 g; yield 58.4%).

Figure 2:
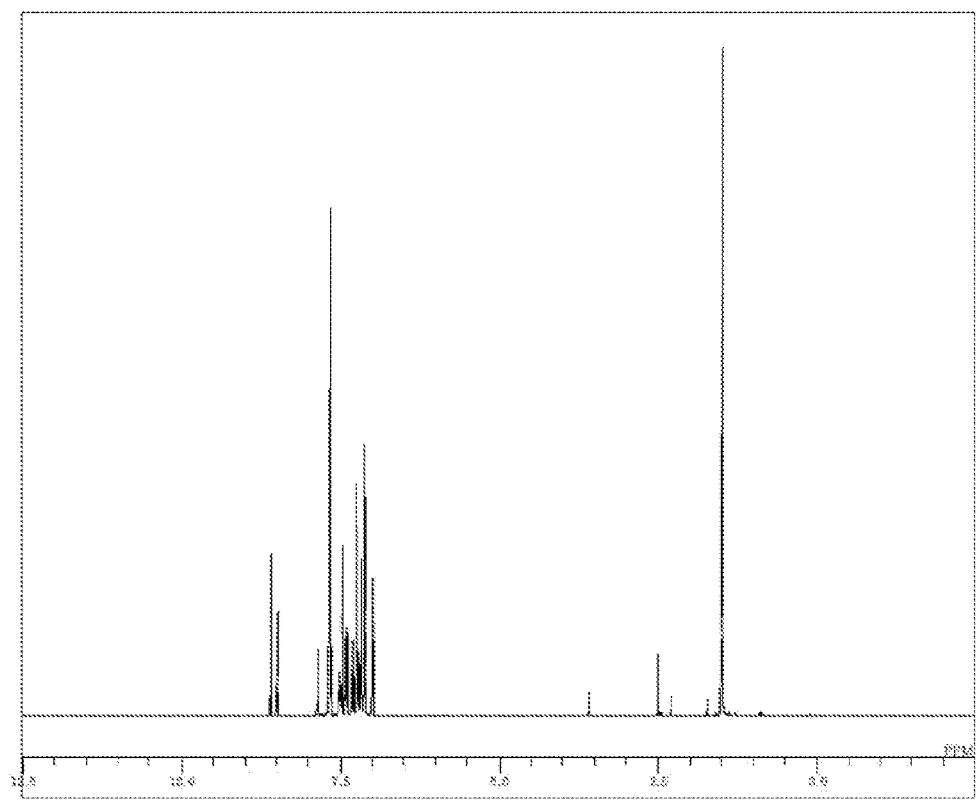
FIG. 2 is a 1H-NMR chart of the compound of Example 2 of the present invention (Compound 6).

The structure of the resulting white powder was identified by NMR. The $^1$H-NMR measurement result is presented in FIG. 2.

$^1$H-NMR (THF-$d_8$) detected 34 hydrogen signals, as follows. δ (ppm)=8.60 (1H), 8.50 (1H), 7.85-7.86 (1H), 7.64-7.69 (7H), 7.48-7.52 (2H), 7.40-7.43 (2H), 7.30-7.32 (1H), 7.24-7.26 (4H), 7.21-7.22 (1H), 7.17-7.18 (2H), 7.11-7.13 (4H), 6.98-7.01 (2H), 1.49 (6H).

Example 3

Synthesis of 12,12,12',12'-tetramethyl-10,10'-diphenyl-10,10',12,12'-tetrahydro-[7,7']bis(indeno[2,1-b]carbazolyl) (Compound 102)

7-Bromo-12,12-dimethyl-10-phenyl-10,12-dihydroindeno[2,1-b]carbazole synthesized in Example 1 (4 g), bis(pinacolato)diboron (2.77 g), potassium acetate (2.69 g), and dimethyl sulfoxide (40 ml) were added to a nitrogen-substituted reaction vessel and aerated with nitrogen gas for 30 min. The mixture was heated after adding a [1,1'-bis(diphenylphosphino)ferrocene]palladium(II)dichloride dichloromethane complex (1:1) (0.22 g), and stirred at 90° C. for 12 hours. After the mixture was cooled to a room temperature, toluene (150 ml) and saturated brine (200 ml) were added to perform liquid separation in order to collect an organic layer. The organic layer was washed three times with saturated brine (100 ml), dehydrated with anhydrous magnesium sulfate, and concentrated under reduced pressure to obtain a crude product. The crude product was purified by column chromatography (carrier: silica gel; eluent: ethyl acetate/n-hexane) to obtain a whitish powder of 12,12-dimethyl-10- phenyl-7-(4,4,5,5-tetramethyl-[1,3,2]dioxaborolan-2-yl)-10,12-dihydroindeno[2,1-b]carbazole (1.89 g; yield 42.7%).

The resulting 12,12-dimethyl-10-phenyl-7-(4,4,5,5-tetramethyl-[1,3,2]dioxaborolan-2-yl)-10,12-dihydroindeno[2,1-b]carbazole (1.8 g), 7-bromo-12,12-dimethyl-10-phenyl-10,12-dihydroindeno[2,1-b]carbazole synthesized in Example 1 (1.55 g), a toluene/ethanol (4/1, v/v) mixed solvent (15 ml), and a 2M potassium carbonate aqueous solution (2.6 ml) were added to a nitrogen-substituted reaction vessel and aerated with nitrogen gas for 30 min under ultrasonic irradiation. The mixture was heated after adding tetrakis(triphenylphosphine)palladium (0.20 g), and stirred at 73° C. for 9 hours. After the mixture was cooled to a room temperature, a precipitated solid was collected by filtration. The precipitate was dissolved by adding tetrahydrofuran (80 ml), and after removing insoluble matter by filtration, a filtrate was concentrated under reduced pressure to obtain a crude product. The crude product was purified by recrystallization using 1,2-dichlorobenzene (10 ml) to obtain a white powder of 12,12,12',12'-tetramethyl-10,10$^1$-diphenyl-10,10',12,12'-tetrahydro-[7,7']bis(indeno[2,1-b]carbazolyl) (1.01 g; yield 39.9%).

Figure 3:
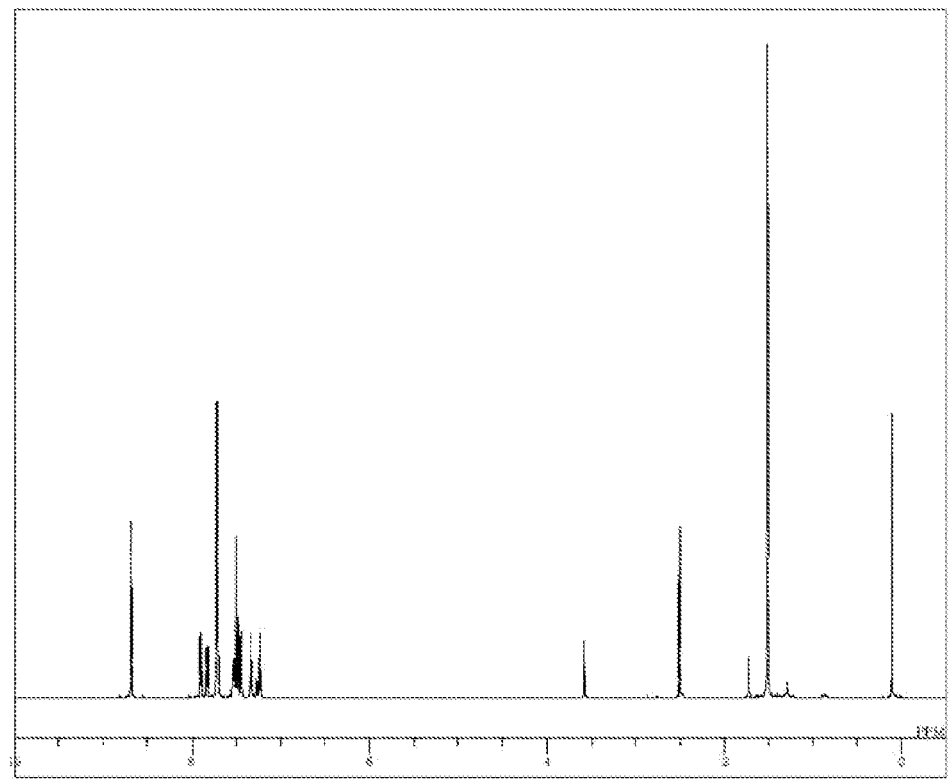
FIG. 3 is a 1H-NMR chart of the compound of Example 3 of the present invention (Compound 102).

The structure of the resulting white powder was identified by NMR. The $^1$H-NMR measurement result is presented in FIG. 3.

$^1$H-NMR (THF-d$_8$) detected 40 hydrogen signals, as follows. δ (ppm)=8.68 (4H), 7.90-7.91 (2H), 7.82-7.84 (2H), 7.69-7.73 (8H), 7.51-7.55 (2H), 7.51 (2H), 7.48-7.49 (2H), 7.44-7.45 (2H), 7.32-7.35 (2H), 7.22-7.25 (2H), 1.52 (12H).

Example 4

Synthesis of 7-[4-{(biphenyl-4-yl)-phenylamino}-phenyl]-12,12-dimethyl-10-phenyl-10,12-dihydroindeno[2,1-b]carbazole (Compound 7)

7-Bromo-12,12-dimethyl-10-phenyl-10,12-dihydro-indeno[2,1-b]carbazole synthesized in Example 1 (3.0 g), (biphenyl-4-yl)-[4-(4,4,5,5-tetramethyl-[1,3,2]dioxaborolan-2-yl)phenyl]-phenylamine (3.7 g), a toluene/ethanol (4/1, v/v) mixed solvent (50 ml), and a 2M potassium carbonate aqueous solution (10 ml) were added to a nitrogen-substituted reaction vessel and aerated with nitrogen gas for 30 min under ultrasonic irradiation. The mixture was heated after adding tetrakis(triphenylphosphine)palladium (0.4 g), and stirred at 73° C. for 8 hours. After the mixture was cooled to a room temperature, a precipitated crude product was collected by filtration. 1,2-Dichlorobenzene (140 ml) was added to the crude product, and the crude product was dissolved while being heated, and after removing insoluble matter by filtration, a filtrate was concentrated under reduced pressure. Purification by recrystallization using 1,2-dichlorobenzene (100 ml) was performed to obtain a white powder of 7-[4-{(biphenyl-4-yl)-phenylamino}-phenyl]-12,12-dimethyl-10-phenyl-10,12-dihydroindeno[2,1-b]carbazole (2.7 g; yield 57.8%).

Figure 4:
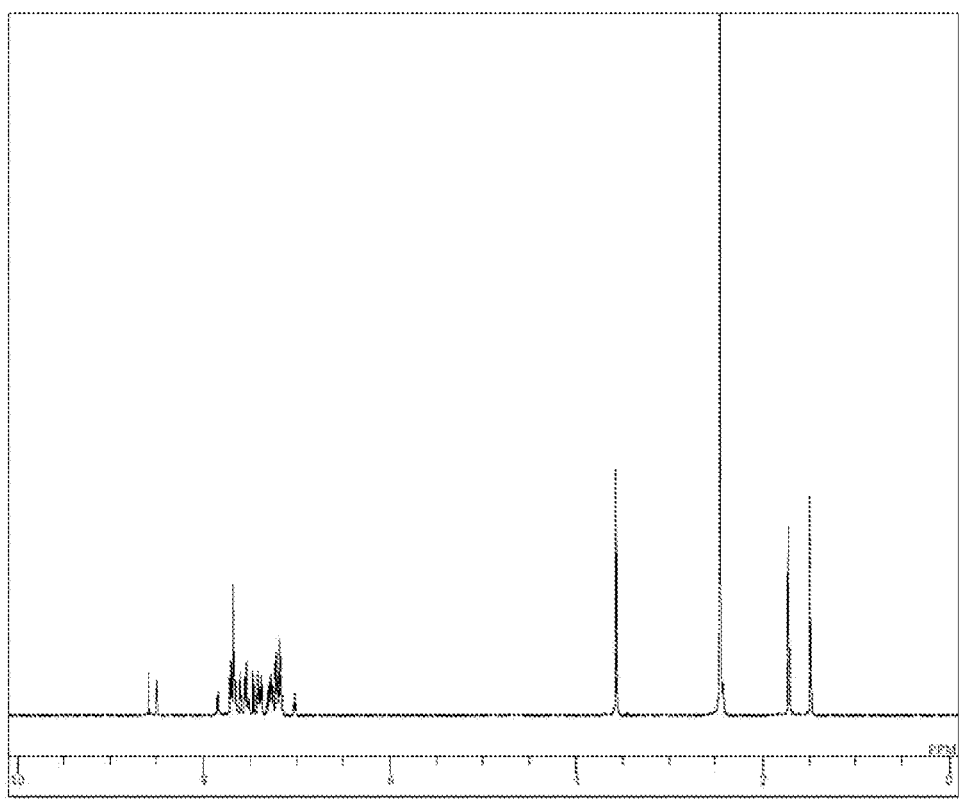
FIG. 4 is a 1H-NMR chart of the compound of Example 4 of the present invention (Compound 7).

The structure of the resulting white powder was identified by NMR. The $^1$H-NMR measurement result is presented in FIG. 4.

$^1$H-NMR (THF-d$_8$) detected 38 hydrogen signals, as follows. δ (ppm)=8.60 (1H), 8.50 (1H), 7.85 (1H), 7.72-7.65 (7H), 7.61 (2H), 7.55 (1H), 7.52 (1H), 7.47 (1H), 7.43-7.37 (4H), 7.31-7.16 (11H), 7.03 (1H), 1.49 (6H).

Example 5

Synthesis of 7-[4-{bis(biphenyl-4-yl)amino}-phenyl]-12,12-dimethyl-10-phenyl-10,12-dihydroindeno[2,1-b]carbazole (Compound 8)

7-Bromo-12,12-dimethyl-10-phenyl-10,12-dihydro-indeno[2,1-b]carbazole synthesized in Example 1 (3.0 g), bis(biphenyl-4-yl)-[4-(4,4,5,5-tetramethyl-[1,3,2]dioxaborolan-2-yl)phenyl]amine (4.3 g), a toluene/ethanol (4/1, v/v) mixed solvent (50 ml), and a 2M potassium carbonate aqueous solution (10 ml) were added to a nitrogen-substituted reaction vessel and aerated with nitrogen gas for 30 min under ultrasonic irradiation. The mixture was heated after adding tetrakis(triphenylphosphine)palladium (0.4 g), and stirred at 73° C. for 8 hours. After the mixture was cooled to a room temperature, a precipitated crude product was collected by filtration. 1,2-dichlorobenzene (140 ml) was added to the crude product, and the crude product was dissolved while being heated, and after removing insoluble matter by filtration, a filtrate was concentrated under reduced pressure. Purification by recrystallization using 1,2-dichlorobenzene (100 ml) was performed to obtain a white powder of 7-[4-{bis(biphenyl-4-yl)amino}-phenyl]-12,12-dimethyl-10-phenyl-10,12-dihydroindeno[2,1-b]carbazole (3.7 g; yield 71.6%).

Figure 5:
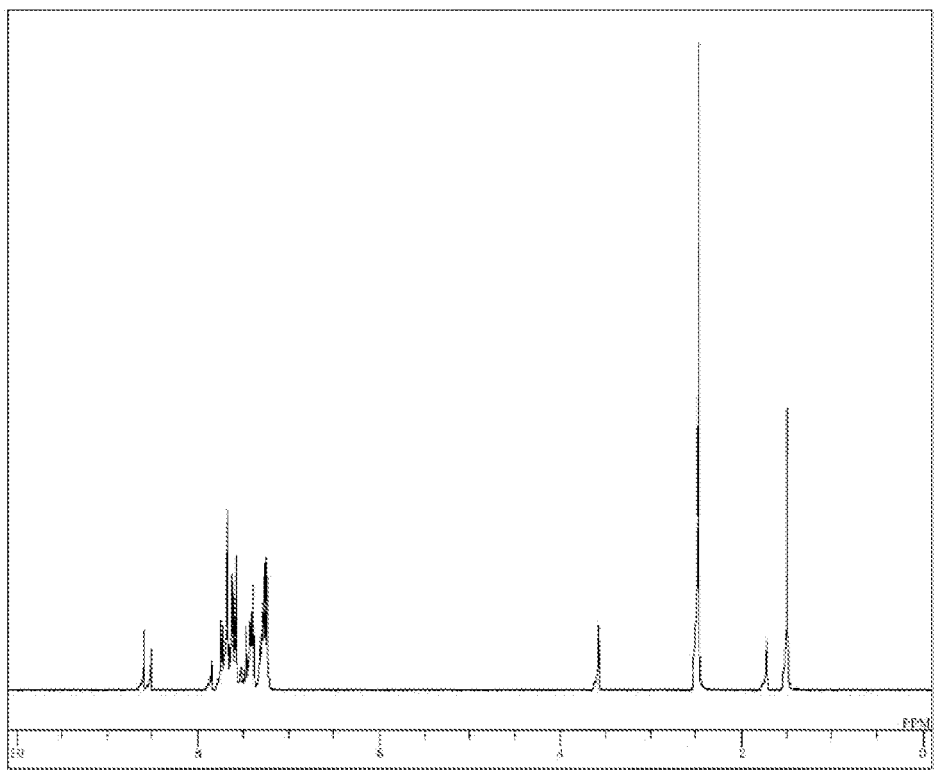
FIG. 5 is a 1H-NMR chart of the compound of Example 5 of the present invention (Compound 8).

The structure of the resulting white powder was identified by NMR. The $^1$H-NMR measurement result is presented in FIG. 5.

$^1$H-NMR (THF-d$_8$) detected 42 hydrogen signals, as follows. δ (ppm)=8.60 (1H), 8.52 (1H), 7.85 (1H), 7.75-7.57 (15H), 7.53 (1H), 7.47 (1H), 7.43-7.38 (6H), 7.32-7.22 (10H), 1.49 (6H).

Example 6

Synthesis of 10-(biphenyl-4-yl)-12,12-dimethyl-7-(9-phenyl-9H-carbazol-3-yl)-10,12-dihydroindeno[2,1-b]carbazole (Compound 122)

12,12-dimethyl-10,12-dihydroindeno[2,1-b]carbazole synthesized in Example 1 (35.5 g), 4-bromobiphenyl (35.0 g), sodium bisulfite (6.0 g), a copper powder (2.4 g), 3,5-di(tert-butyl)salicylic acid (9.4 g), potassium carbonate (31.2 g), and dodecylbenzene (52 ml) were added to a nitrogen-substituted reaction vessel, heated, and stirred at 190° C. for 26 hours. After cooled to 120° C., the mixture was stirred after adding toluene (35 ml), and a crude product was collected by filtration. After adding toluene (1.6 L) to the crude product, the crude product was heated and extracted at 110° C. After cooled to a room temperature, the crude product was concentrated under reduced pressure. The product was crystallized with methanol (120 ml) to obtain a white powder of 10-(biphenyl-4-yl)-12,12-dimethyl-10,12-dihydroindeno[2,1-b]carbazole (48.5 g; yield 88.1%).

The resulting 10-(biphenyl-4-yl)-12,12-dimethyl-10,12-dihydroindeno[2,1-b]carbazole (42.5 g) and DMF (2.5 L) were added to a reaction vessel, and the mixture was heated up to 70° C. and dissolved. After cooled to a room temperature, N-bromo-succinimide (17.4 g) was added, and the mixture was stirred for 7 hours. Water (2.5 L) was added, and filtration was performed to obtain a white powder of 10-(biphenyl-4-yl)-7-bromo-12,12-dimethyl-10,12-dihydroindeno[2,1-b]carbazole (34.9 g; yield 69.5%).

The resulting 10-(biphenyl-4-yl)-7-bromo-12,12-dimethyl-10,12-dihydroindeno[2,1-b]carbazole (16.5 g), 9-phenyl-3-(4,4,5,5-tetramethyl-1,3,2-dioxaborolan-2-yl)-9H-carbazole (14.2 g), a toluene/ethanol (4/1, v/v) mixed solvent (250 ml), and a 2M potassium carbonate aqueous solution (48 ml) were added to a nitrogen-substituted reaction vessel and aerated with nitrogen gas for 30 min under ultrasonic irradiation. The mixture was heated after adding tetrakis(triphenylphosphine)palladium (1.9 g), and stirred at 73° C. for 5 hours. After the mixture was cooled to a room temperature, a precipitated crude product was collected by filtration. 1,2-Dichlorobenzene (450 ml) was added to the crude product, and the crude product was dissolved while being heated, and after removing insoluble matter by filtration, a filtrate was concentrated under reduced pressure. Purification by crystallization using 1,2-dichlorobenzene (150 ml) and n-hexane (300 ml) was performed to obtain a white powder of 10-(biphenyl-4-yl)-12,12-dimethyl-7-(9-phenyl-9H-carbazol-3-yl)-10,12-dihydroindeno[2,1-b]carbazole (9.8 g; yield 45.2%).

Figure 6:
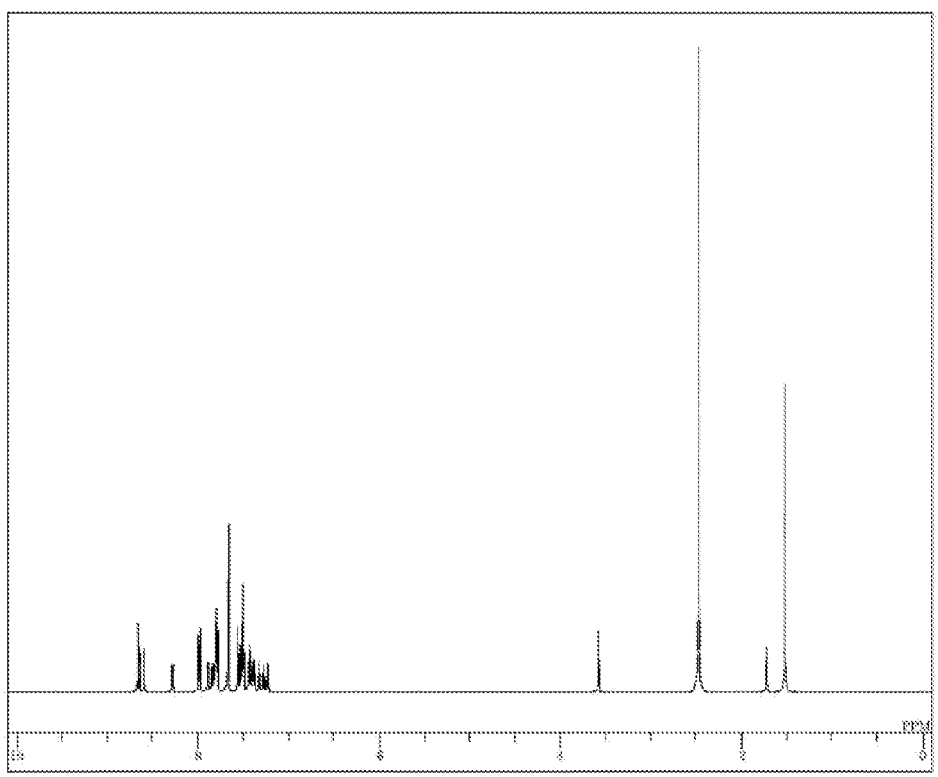
FIG. 6 is a 1H-NMR chart of the compound of Example 6 of the present invention (Compound 122).

The structure of the resulting white powder was identified by NMR. The $^1$H-NMR measurement result is presented in FIG. 6.

$^1$H-NMR (THF-$d_8$) detected 36 hydrogen signals, as follows. δ (ppm)=8.69 (1H), 8.64 (1H), 8.59 (1H), 8.28 (1H), 7.99 (2H), 7.89 (1H), 7.85-7.78 (6H), 7.66 (4H), 7.56-7.49 (6H), 7.44-7.37 (4H), 7.32 (1H), 7.27 (1H), 7.23 (1H), 1.52 (6H).

Example 7

Synthesis of 10-(biphenyl-4-yl)-7-[4-bis(biphenyl-4-yl)amino-phenyl]-12,12-dimethyl-10,12-dihydroindeno[2,1-b]carbazole (Compound 123)

10-(biphenyl-4-yl)-7-bromo-12,12-dimethyl-10,12-dihydroindeno[2,1-b]carbazole synthesized in Example 6 (13.0 g), bis(biphenyl-4-yl)-[4-(4,4,5,5-tetramethyl-[1,3,2]dioxaborolan-2-yl)phenyl]amine (15.9 g) a toluene/ethanol (4/1, v/v) mixed solvent (250 ml), and a 2M potassium carbonate aqueous solution (51 ml) were added to a nitrogen-substituted reaction vessel and aerated with nitrogen gas for 30 min under ultrasonic irradiation. The mixture was heated after adding tetrakis(triphenylphosphine)palladium (2.1 g), and stirred at 73° C. for 10 hours. After the mixture was cooled to a room temperature, a precipitated crude product was collected by filtration. 1,2-Dichlorobenzene (1.7 L) was added to the crude product, and the crude product was dissolved while being heated, and after removing insoluble matter by filtration, a filtrate was cooled to a room temperature. A precipitated solid was collected by filtration and purified by recrystallization using 1,2-dichlorobenzene (1.7 L) to obtain a white powder of 10-(biphenyl-4-yl)-7-[4-bis(biphenyl-4-yl)amino-phenyl]-12,12-dimethyl-10,12-dihydroindeno[2,1-b]carbazole (13.4 g; yield 63.8%).

Figure 7:
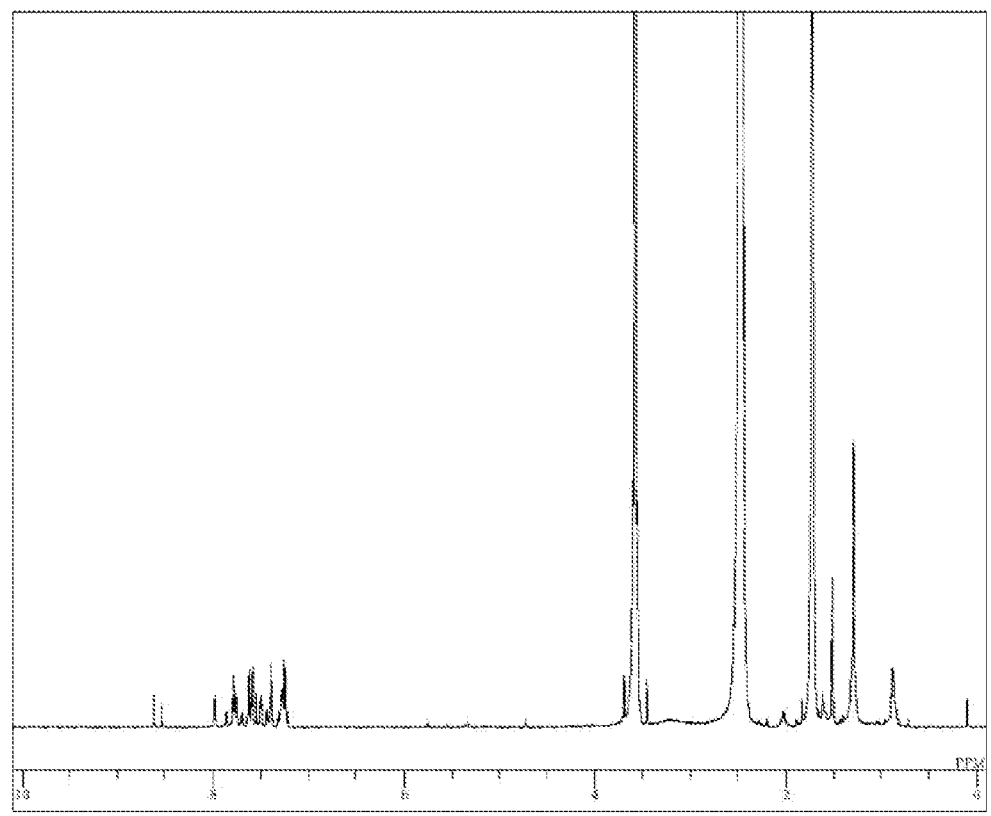
FIG. 7 is a 1H-NMR chart of the compound of Example 7 of the present invention (Compound 123).

The structure of the resulting white powder was identified by NMR. The $^1$H-NMR measurement result is presented in FIG. 7.

$^1$H-NMR (THF-$d_8$) detected 46 hydrogen signals, as follows. δ (ppm)=8.62 (1H), 8.54 (1H), 7.98 (2H), 7.86 (1H), 7.78 (4H), 7.75 (2H), 7.70 (1H), 7.63 (4H), 7.58 (4H), 7.55 (1H), 7.50 (3H), 7.43 (1H), 7.40 (4H), 7.33-7.21 (11H), 1.51 (6H).

Example 8

Synthesis of 12,12-dimethyl-10-(9,9-dimethyl-9H-fluorene-2-yl)-7-(9-phenyl-9H-carbazol-3-yl)-10,12-dihydroindeno[2,1-b]carbazole (Compound 124)

12,12-Dimethyl-10,12-dihydroindeno[2,1-b]carbazole synthesized in Example 1 (5.5 g), 2-bromo-9,9-dimethyl-9H-fluorene (6.4 g), sodium bisulfite (0.3 g), a copper powder (0.1 g), 3,5-di(tert-butyl)salicylic acid (0.5 g), potassium carbonate (4.0 g), and dodecylbenzene (5 ml) were added to a nitrogen-substituted reaction vessel, heated, and stirred at 180° C. for 29 hours. The mixture was cooled to 100° C., and insoluble matter was removed by filtration after adding toluene (80 ml), and a filtrate was concentrated. Crystallization using n-hexane (20 ml) was performed to obtain an ocher powder of 12,12-dimethyl-10-(9,9-dimethyl-9H-fluorene-2-yl)-10,12-dihydroindeno[2,1-b]carbazole (7.4 g; yield 80.0%)

The resulting 12,12-dimethyl-10-(9,9-dimethyl-9H-fluorene-2-yl)-10,12-dihydroindeno[2,1-b]carbazole (7.0 g) and DMF (140 ml) were added to a reaction vessel. The mixture was heated up to 100° C., dissolved, and cooled. N-bromosuccinimide (2.6 g) was added under ice-cooled conditions, and the mixture was stirred for 1 hour at a room temperature. Water (500 ml) was added, and the mixture was subjected to filtration to obtain a pale red powder of 7-bromo-12,12-dimethyl-10-(9,9-dimethyl-9H-fluorene-2-yl)-10,12-dihydroindeno[2,1-b]carbazole (5.7 g; yield 70.3%).

The resulting 7-bromo-12,12-dimethyl-10-(9,9-dimethyl-9H-fluorene-2-yl)-10,12-dihydroindeno[2,1-b]carbazole (4.0 g), 9-phenyl-3-(4,4,5,5-tetramethyl-1,3,2-dioxaborolan-2-yl)-9H-carbazole (3.2 g), a toluene/ethanol (4/1, v/v) mixed solvent (50 ml), and a 2M potassium carbonate aqueous solution (10 ml) were added to a nitrogen-substituted reaction vessel and aerated with nitrogen gas for 30 min under ultrasonic irradiation. The mixture was heated after adding tetrakis(triphenylphosphine)palladium (0.4 g), and stirred at 71° C. for 7 hours. After the mixture was cooled to a room temperature, water (20 ml) was added to perform liquid separation in order to collect an organic layer. The organic layer was dehydrated with anhydrous magnesium sulfate and concentrated under reduced pressure to obtain a crude product. The crude product was purified by column chromatography (carrier: silica gel; eluent: toluene/cyclohexane) to obtain a white powder of 12,12-dimethyl-10-(9,9-dimethyl-9H-fluorene-2-yl)-7-(9-phenyl-9H-carbazole-3-yl)-10,12-dihydroindeno[2,1-b]carbazole (3.4 g; yield 65.7%).

Figure 8:
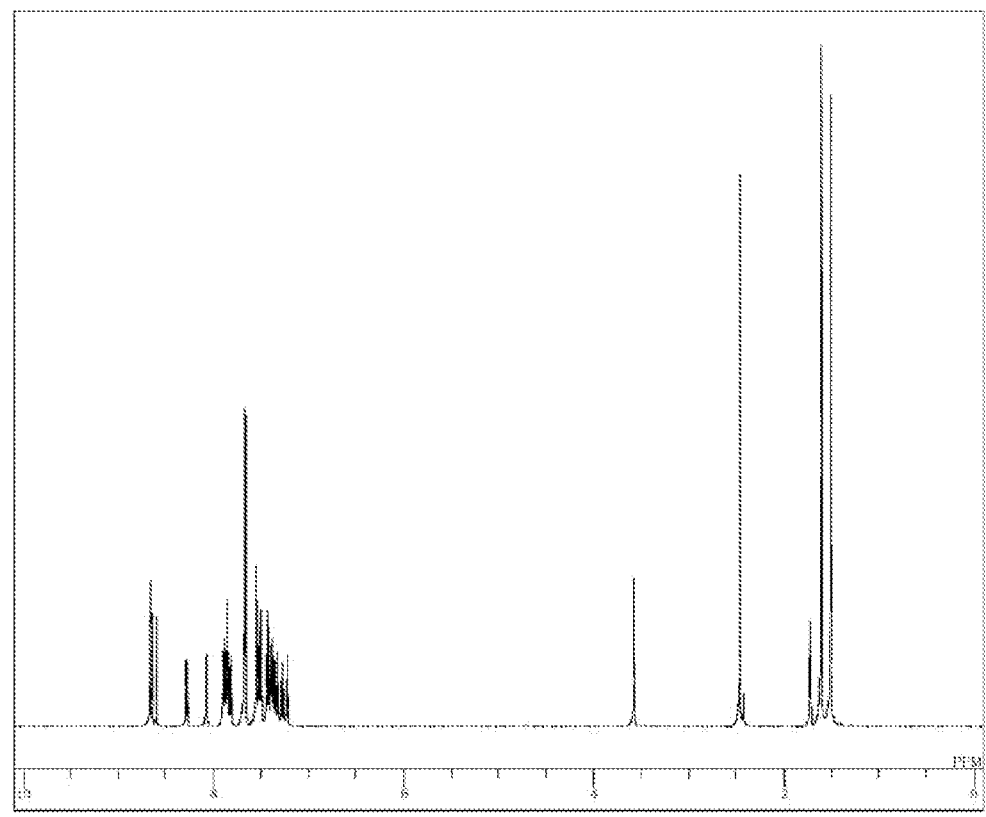
FIG. 8 is a 1H-NMR chart of the compound of Example 8 of the present invention (Compound 124).

The structure of the resulting white powder was identified by NMR. The $^1$H-NMR measurement result is presented in FIG. 8.

$^1$H-NMR (THF-$d_8$) detected 40 hydrogen signals, as follows. δ (ppm)=8.67 (1H), 8.65 (1H), 8.60 (1H), 8.28 (1H), 8.08 (1H), 7.90-7.82 (5H), 7.69-7.66 (5H), 7.58-7.49 (5H), 7.43 (2H), 7.39 (2H), 7.36 (1H), 7.33 (1H), 7.28 (1H), 7.23 (1H), 1.61 (6H), 1.51 (6H).

Example 9

The glass transition point of the compounds of the present invention were determined using a high-sensitive differential scanning calorimeter (DSC 3100S produced by Bruker AXS).

|  | Glass transition point |
| --- | --- |
| Compound of Example 1 of the present invention | 148° C. |
| Compound of Example 2 of the present invention | 132° C. |
| Compound of Example 3 of the present invention | 158° C. |
| Compound of Example 4 of the present invention | 143° C. |

-continued

| | Glass transition point |
|---|---|
| Compound of Example 5 of the present invention | 162° C. |
| Compound of Example 6 of the present invention | 163° C. |
| Compound of Example 7 of the present invention | 170° C. |
| Compound of Example 8 of the present invention | 173° C. |

The compounds of the present invention have glass transition points of 100° C. or higher, demonstrating that the compounds of the present invention have a stable thin-film state.

Example 10

A 100 nm-thick vapor-deposited film was fabricated on an ITO substrate using the compounds of the present invention, and a work function was measured using an atmosphere photoelectron spectrometer (Model AC-3 produced by Riken Keiki Co., Ltd.).

| | Work function |
|---|---|
| Compound of Example 1 of the present invention | 5.59 eV |
| Compound of Example 2 of the present invention | 5.50 eV |
| Compound of Example 3 of the present invention | 5.50 eV |
| Compound of Example 4 of the present invention | 5.45 eV |
| Compound of Example 5 of the present invention | 5.44 eV |
| Compound of Example 6 of the present invention | 5.56 eV |
| Compound of Example 7 of the present invention | 5.59 eV |
| Compound of Example 8 of the present invention | 5.58 eV |

As the results show, the compounds of the present invention have desirable energy levels compared to the work function 5.4 eV of common hole transport materials such as NPD and TPD, and thus possess desirable hole transportability.

Example 11

Figure 9:
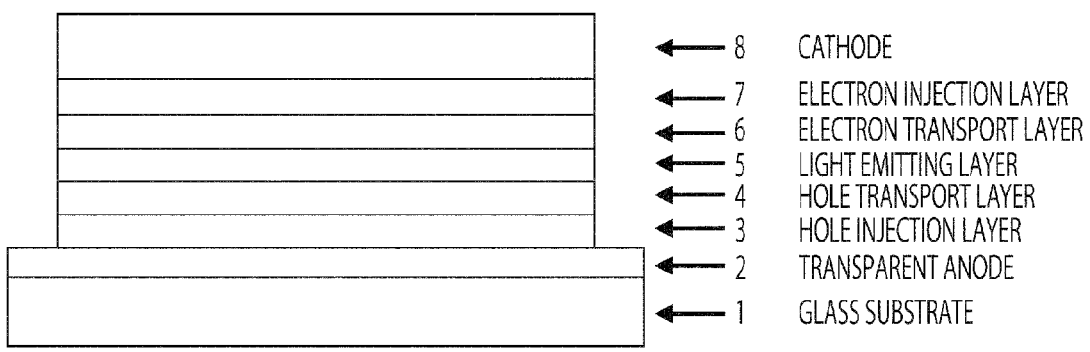
FIG. 9 is a diagram illustrating the configuration of the EL devices of Examples 11 to 17 and Comparative Examples 1 and 2.

An organic EL device, as illustrated in FIG. 9, was fabricated by forming a hole injection layer 3, a hole transport layer 4, a light emitting layer 5, an electron transport layer 6, an electron injection layer 7, and a cathode (an aluminum electrode) 8 in this order by vapor deposition on a glass substrate 1 that had been provided beforehand with an ITO electrode as a transparent anode 2.

Specifically, the glass substrate 1 with ITO formed with a film thickness of 150 nm thereon was washed with an organic solvent and subjected to an oxygen plasma treatment to wash the surface. The glass substrate with the ITO electrode was then installed in a vacuum vapor deposition apparatus, and the pressure was reduced to 0.001 Pa or less. This was followed by the formation of the hole injection layer 3 by forming Compound 125 of the structural formula below over the transparent anode 2 in a film thickness of 20 nm. The hole transport layer 4 was then formed on the hole injection layer 3 by forming the compound of Example 1 of the present invention (Compound 5) in a film thickness of 40 nm. Thereafter, the light emitting layer 5 was formed on the hole transport layer 4 by forming Compounds 126 and 127 of the structural formulae below in a film thickness of 30 nm using dual vapor deposition at a deposition rate ratio of Compound 126:Compound 127=5:95. Then, the electron transport layer 6 was formed on the light emitting layer 5 by forming $Alq_3$ in a film thickness of 30 nm. The electron injection layer 7 was then formed on the electron transport layer 6 by forming lithium fluoride in a film thickness of 0.5 nm. Finally, the cathode 8 was formed by vapor-depositing aluminum in a film thickness of 150 nm. The characteristics of the organic EL device thus fabricated were measured in the atmosphere at an ordinary temperature.

Table 1 summarizes the results of the emission characteristics measurements performed by applying a DC voltage to the organic EL device produced by using the compound of Example 1 of the present invention (Compound 5).

[Chemical Formula 131]

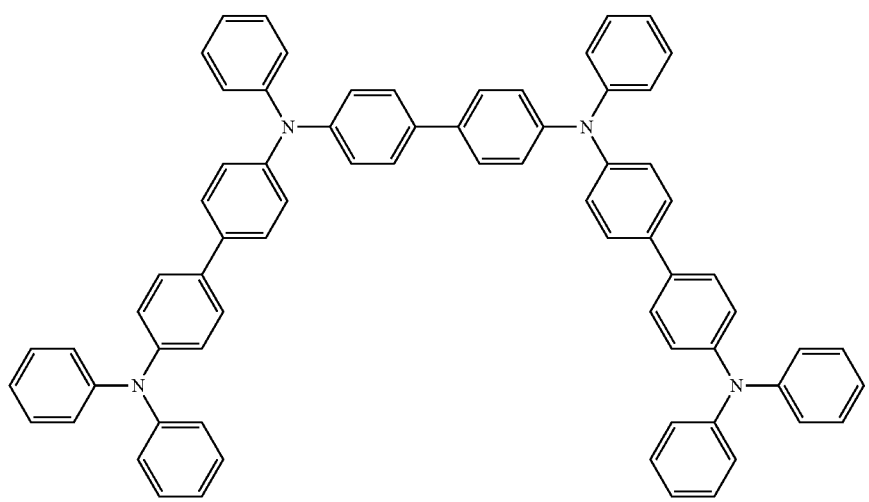

(Compound 125)

[Chemical Formula 132]

(Compound 126)

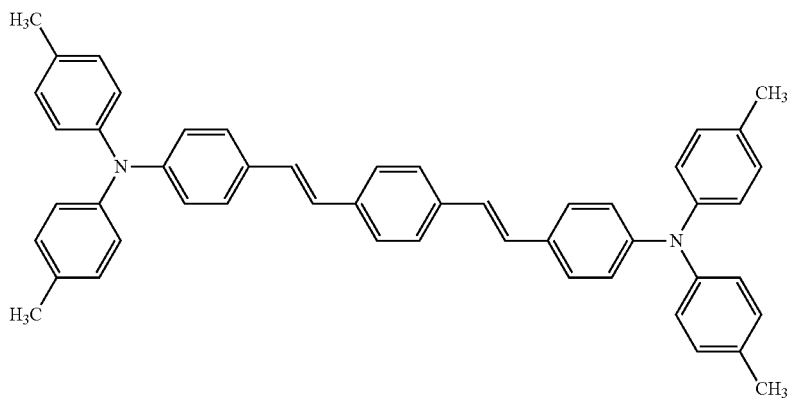

[Chemical Formula 133]

(Compound 127)

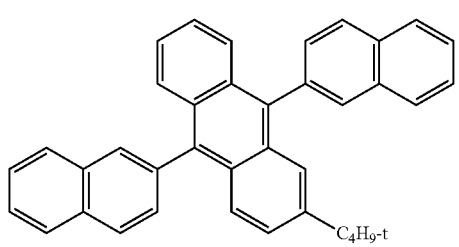

Example 12

An organic EL device was fabricated under the same conditions used in Example 11, except that the compound of Example 2 of the present invention (Compound 6) was used as the material of the hole transport layer 4 in Example 11. The characteristics of the organic EL device thus fabricated were measured in the atmosphere at an ordinary temperature. Table 1 summarizes the results of the emission characteristics measurements performed by applying a DC voltage to the fabricated organic EL device.

Example 13

An organic EL device was fabricated under the same conditions used in Example 11, except that the compound of Example 4 of the present invention (Compound 7) was used as the material of the hole transport layer 4 in Example 11. The characteristics of the organic EL device thus fabricated were measured in the atmosphere at an ordinary temperature. Table 1 summarizes the results of the emission characteristics measurements performed by applying a DC voltage to the fabricated organic EL device.

Example 14

An organic EL device was fabricated under the same conditions used in Example 11, except that the compound of Example 5 of the present invention (Compound 8) was used as the material of the hole transport layer 4 in Example 11. The characteristics of the organic EL device thus fabricated were measured in the atmosphere at an ordinary temperature. Table 1 summarizes the results of the emission characteristics measurements performed by applying a DC voltage to the fabricated organic EL device.

Example 15

An organic EL device was fabricated under the same conditions used in Example 11, except that the compound of Example 6 of the present invention (Compound 122) was used as the material of the hole transport layer 4 in Example 11. The characteristics of the organic EL device thus fabricated were measured in the atmosphere at an ordinary temperature. Table 1 summarizes the results of the emission characteristics measurements performed by applying a DC voltage to the fabricated organic EL device.

Example 16

An organic EL device was fabricated under the same conditions used in Example 11, except that the compound of Example 7 of the present invention (Compound 123) was used as the material of the hole transport layer 4 in Example 11. The characteristics of the organic EL device thus fabricated were measured in the atmosphere at an ordinary temperature. Table 1 summarizes the results of the emission characteristics measurements performed by applying a DC voltage to the fabricated organic EL device.

Example 17

An organic EL device was fabricated under the same conditions used in Example 11, except that the compound of Example 8 of the present invention (Compound 124) was used as the material of the hole transport layer 4 in Example 11. The characteristics of the organic EL device thus fabricated were measured in the atmosphere at an ordinary temperature. Table 1 summarizes the results of the emission characteristics measurements performed by applying a DC voltage to the fabricated organic EL device.

Comparative Example 1

For comparison, an organic EL device was fabricated under the same conditions used in Example 11, except that the Compound B was used as the material of the hole transport layer 4 in Example 11. The characteristics of the organic EL device thus fabricated were measured in the atmosphere at an ordinary temperature. Table 1 summarizes the results of the emission characteristics measurements performed by applying a DC voltage to the fabricated organic EL device.

Comparative Example 2

For comparison, an organic EL device was fabricated under the same conditions used in Example 11, except that Compound 128 of the structural formula below was used as the material of the hole transport layer 4 in Example 11. The characteristics of the organic EL device thus fabricated were measured in the atmosphere at an ordinary temperature. Table 1 summarizes the results of the emission characteristics measurements performed by applying a DC voltage to the fabricated organic EL device.

[Chemical Formula 134]

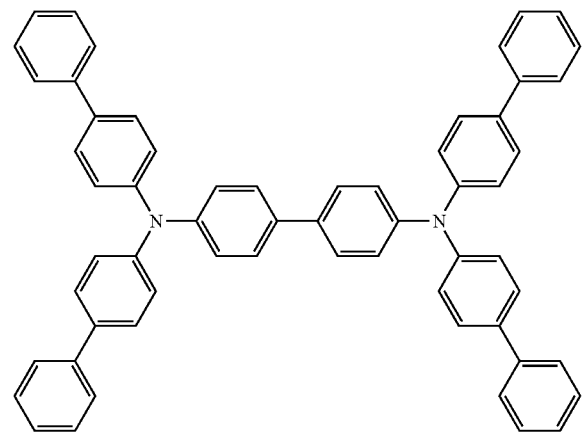

(Compound 128)

As shown in Table 1, the driving voltage when applying a current with a current density of 10 mA/cm² was 4.77 to 5.46 V for the compounds of Examples 1 to 2 and 4 to 8 of the present invention (Compounds 5 to 8 and 122 to 124), which was lower than 5.62 V of Compound B.

The power efficiency of the compounds of Examples 1 to 2 and 4 to 8 in the present invention (Compounds 5 to 8 and 122 to 124) was 5.30 to 6.34 lm/W, which showed great improvement over the power efficiency 5.06 lm/W of Compound B.

Further, when compared to the power efficiency 5.49 lm/W of Compound 128, there was improvement in the compounds of Examples 6 to 8 in the present invention (Compounds 122 to 124) as shown in their power efficiency 5.64 to 6.76 lm/W, and there was a great improvement particularly in the compounds of Examples 1 to 2 and 4 to 5 in the present invention (Compounds 5 to 8) as shown in their power efficiency 5.84 to 6.34 lm/W.

As the above results clearly demonstrate, the organic EL devices using the compounds having an indenocarbazole ring structure in the present invention has achieved improvement in power efficiency, and a lower actual driving voltage compared to the organic EL device using the known Compound B.

It was also found that the power efficiency can be improved over the organic EL device using Compound 128 known as a hole transport material of high performance.

INDUSTRIAL APPLICABILITY

The compounds having an indenocarbazole ring structure of the present invention have high hole transportability, excel in electron blocking ability and amorphousness, and have a stable thin-film state. The compounds are therefore excellent as the compounds for organic EL devices. The organic EL devices fabricated with the compounds can have high luminous efficiency and high power efficiency and can have a low actual driving voltage to improve durability. There are potential applications for, for example, home electric appliances and illuminations.

DESCRIPTION OF REFERENCE NUMERAL

1 Glass substrate
2 Transparent anode
3 Hole injection layer
4 Hole transport layer

TABLE 1

| | Compound | Voltage [V] (@10 mA/cm²) | Luminance [cd/m²] (@10 mA/cm²) | Current efficiency [cd/A] (@10 mA/cm²) | Power efficiency [l m/W] (@10 mA/cm²) |
|---|---|---|---|---|---|
| Ex. 11 | Compound 5 | 5.35 | 993 | 9.93 | 5.84 |
| Ex. 12 | Compound 6 | 5.08 | 964 | 9.65 | 5.97 |
| Ex. 13 | Compound 7 | 4.77 | 963 | 9.63 | 6.34 |
| Ex. 14 | Compound 8 | 4.97 | 962 | 9.62 | 6.09 |
| Ex. 15 | Compound 122 | 5.46 | 975 | 9.75 | 5.64 |
| Ex. 16 | Compound 123 | 5.28 | 957 | 9.57 | 5.70 |
| Ex. 17 | Compound 124 | 5.36 | 980 | 9.80 | 5.76 |
| Com. Ex. 1 | Compound B | 5.62 | 908 | 9.07 | 5.06 |
| Com. Ex. 2 | Compound 128 | 5.17 | 902 | 9.03 | 5.49 |

5 Light emitting layer
6 Electron transport layer
7 Electron injection layer
8 Cathode

The invention claimed is:

1. A compound of the following general formula (1) having an indenocarbazole ring structure,

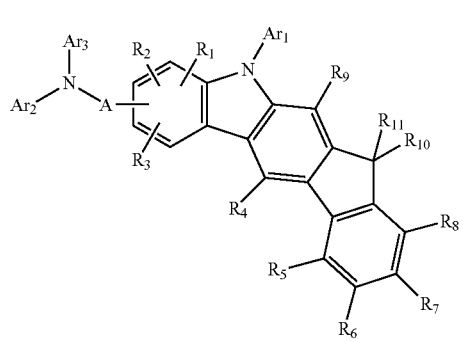

(1)

wherein A represents a divalent group of a substituted or unsubstituted aromatic hydrocarbon, a divalent group of a substituted or unsubstituted aromatic heterocyclic ring, or a divalent group of substituted or unsubstituted condensed polycyclic aromatics; $Ar_1$, $Ar_2$, and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group, where A and $Ar_2$, or $Ar_2$ and $Ar_3$ may bind to each other via a single bond or via substituted or unsubstituted methylene, an oxygen atom, or a sulfur atom to form a ring; $R_1$ to $R_9$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring; and $R_{10}$ and $R_{11}$ may be the same or different, and represent linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

2. The compound having an indenocarbazole ring structure according to claim 1, wherein the compound is represented by the following general formula (2),

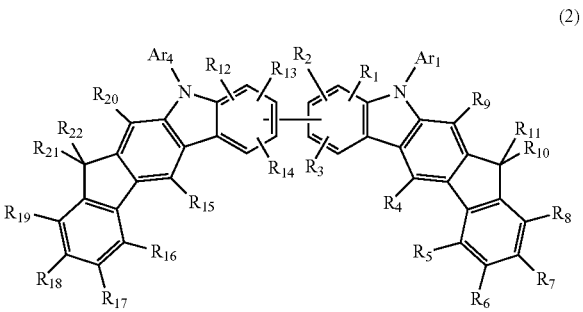

(2)

wherein $Ar_1$ and $Ar_4$ may be the same or different, and represent a substituted or unsubstituted aromatic hydrocarbon group, a substituted or unsubstituted aromatic heterocyclic group, or a substituted or unsubstituted condensed polycyclic aromatic group; $R_1$ to $R_9$ and $R_{12}$ to $R_{20}$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring; and $R_{10}$, $R_{11}$, $R_{21}$, and $R_{22}$ may be the same or different, and represent linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where $R_{10}$ and $R_{11}$, or $R_{21}$ and $R_{22}$ may bind to each other via a single bond, substituted or unsubstituted methylene, an oxygen atom, or a sulfur atom to form a ring.

3. The compound having an indenocarbazole ring structure according to claim 2, wherein the compound is represented by the following general formula (4), (4)

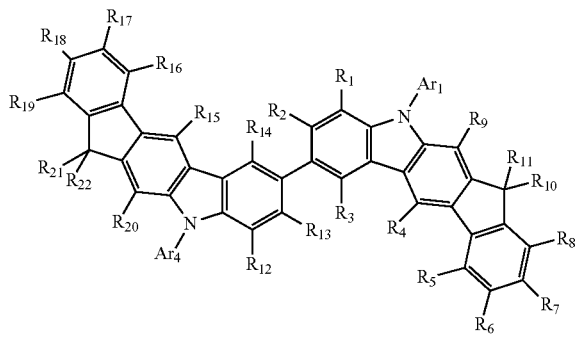

wherein Ar₁ and Ar₄ may be the same or different, and represent a substituted or unsubstituted aromatic hydrocarbon group, a substituted or unsubstituted aromatic heterocyclic group, or a substituted or unsubstituted condensed polycyclic aromatic group; $R_1$ to $R_9$ and $R_{12}$ to $R_{20}$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring; and $R_{10}$, $R_{11}$, $R_{21}$, and $R_{22}$ may be the same or different, and represent linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where $R_{10}$ and $R_{11}$, or $R_{21}$ and $R_{22}$ may bind to each other via a single bond, substituted or unsubstituted methylene, an oxygen atom, or a sulfur atom to form a ring.

4. The compound having an indenocarbazole ring structure according to claim 3, wherein $R_{10}$, $R_{11}$, $R_{21}$, and $R_{22}$ in the general formula (2) or (4) represent linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent.

5. The compound having an indenocarbazole ring structure according to claim 2, wherein $R_{10}$, $R_{11}$, $R_{21}$, and $R_{22}$ in the general formula (2) or (4) represent linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent.

6. The compound having an indenocarbazole ring structure according to claim 1, wherein the compound is represented by the following general formula (3), (3)

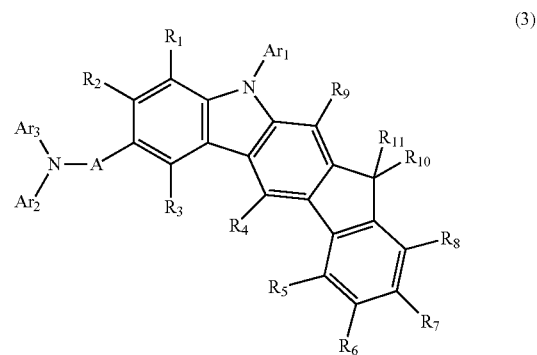

wherein A represents a divalent group of a substituted or unsubstituted aromatic hydrocarbon, a divalent group of a substituted or unsubstituted aromatic heterocyclic ring, or a divalent group of substituted or unsubstituted condensed polycyclic aromatics; $Ar_1$, $Ar_2$, and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group, where A and $Ar_2$, or $Ar_2$ and $Ar_3$ may bind to each other via a single bond or via substituted or unsubstituted methylene, an oxygen atom, or a sulfur atom to form a ring; $R_1$ to $R_9$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring; and $R_{10}$ and $R_{11}$ may be the same or different, and represent linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

7. The compound having an indenocarbazole ring structure according to claim 6, wherein A in the general formula (3) represents substituted or unsubstituted phenylene.

8. The compound having an indenocarbazole ring structure according to claim 6, wherein the compound is represented by the following general formula (3-1),

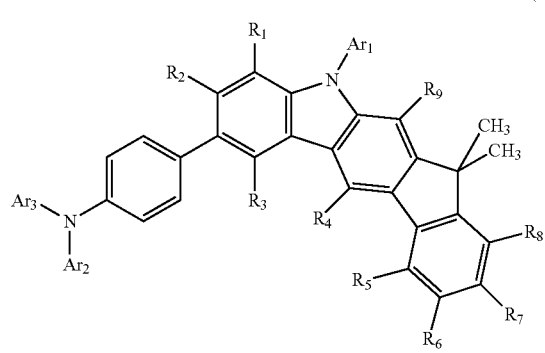

(3-1)

wherein $Ar_1$, $Ar_2$, and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group; and $R_1$ to $R_9$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

9. The compound having an indenocarbazole ring structure according to claim 8, wherein the compound is represented by the following general formula (3-2),

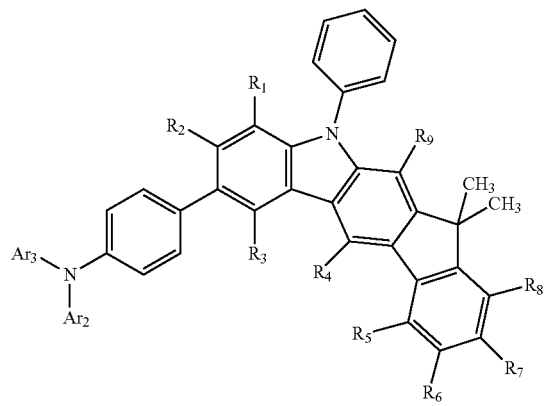

(3-2)

wherein $Ar_2$ and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group; and $R_1$ to $R_9$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

10. The compound having an indenocarbazole ring structure according to claim 6, wherein the compound is represented by the following general formula (3-3),

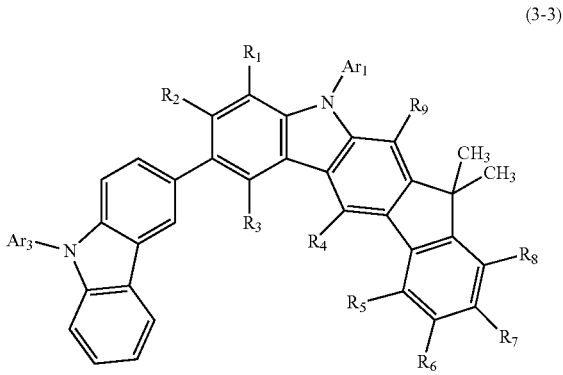

(3-3)

wherein $Ar_1$ and $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group; and $R_1$ to $R_9$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

11. The compound having an indenocarbazole ring structure according to claim 10, wherein the compound is represented by the following general formula (3-4), (3-4)

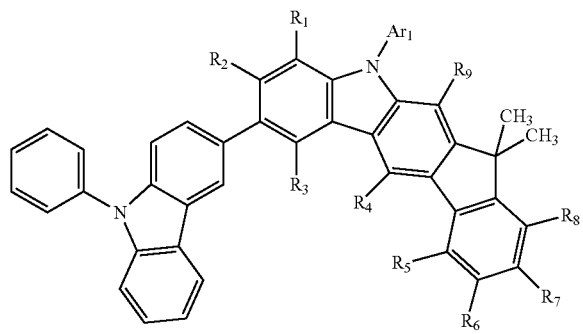

wherein Ar₁ represents a substituted or unsubstituted aromatic hydrocarbon group, a substituted or unsubstituted aromatic heterocyclic group, or a substituted or unsubstituted condensed polycyclic aromatic group; and $R_1$ to $R_9$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other via a single bond, substituted or unsubstituted methylene, an oxygen atom, or a sulfur atom to form a ring.

12. The compound having an indenocarbazole ring structure according to claim 6, wherein $R_{10}$ and $R_{11}$ in the general formula (1) or (3) represent linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent.

13. The compound having an indenocarbazole ring structure according to claim 1, wherein $R_{10}$ and $R_{11}$ in the general formula (1) or (3) represent linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent.

14. An organic electroluminescent device that comprises a pair of electrodes, and one or more organic layers sandwiched between the pair of electrodes,
wherein the compound having an indenocarbazole ring structure of claim 1 is used as a constituent material of at least one organic layer.

15. The organic electroluminescent device according to claim 14, wherein the organic layer is a hole transport layer.

16. The organic electroluminescent device according to claim 14, wherein the organic layer is an electron blocking layer.

17. The organic electroluminescent device according to claim 14, wherein the organic layer is a hole injection layer.

18. The organic electroluminescent device according to claim 14, wherein the organic layer is a light emitting layer.

* * * * *